United States Patent
Khomami Abadi et al.

(10) Patent No.: US 11,106,977 B2
(45) Date of Patent: Aug. 31, 2021

(54) SYSTEMS AND METHODS FOR LEARNING ACROSS MULTIPLE CHEMICAL SENSING UNITS USING A MUTUAL LATENT REPRESENTATION

(71) Applicant: Stratuscent Inc., Montreal (CA)

(72) Inventors: Mojtaba Khomami Abadi, Montreal (CA); Amir Bahador Gahroosi, Montreal (CA); Ashok Prabhu Masilamani, Montreal (CA); Neven Maric, Montreal (CA)

(73) Assignee: Stratuscent Inc., Montreal (CA)

( * ) Notice: Subject to any disclaimer, the term of this patent is extended or adjusted under 35 U.S.C. 154(b) by 0 days.

(21) Appl. No.: 16/797,740

(22) Filed: Feb. 21, 2020

(65) Prior Publication Data

US 2020/0272900 A1    Aug. 27, 2020

Related U.S. Application Data

(60) Provisional application No. 62/809,364, filed on Feb. 22, 2019.

(51) Int. Cl.
*G06N 3/08* (2006.01)
*G16C 20/70* (2019.01)
*G06N 3/04* (2006.01)

(52) U.S. Cl.
CPC ............. *G06N 3/08* (2013.01); *G06N 3/0454* (2013.01); *G16C 20/70* (2019.02)

(58) Field of Classification Search
CPC ......... G16C 20/70; G06N 3/0454; G06N 3/08
See application file for complete search history.

(56) References Cited

U.S. PATENT DOCUMENTS 6,411,905 B1 * 6/2002 Guoliang ........... G01N 33/0001
                                                     702/23
6,649,416 B1    11/2003 Kauer et al.
(Continued)

FOREIGN PATENT DOCUMENTS

EP    1 130 382 A1    9/2001

OTHER PUBLICATIONS

Steven Kearnes, "Molecular graph convolutions: moving beyond fingerprints", J Comput Aided Mol Des (2016) 30:595-608 (Year: 2016).*

(Continued)

*Primary Examiner* — Yoshihisa Ishizuka
(74) *Attorney, Agent, or Firm* — Wolf, Greenfield & Sacks, P.C.

(57) ABSTRACT

Systems and methods for training models across multiple sensing units in a chemical sensing system are described. The chemical sensing system comprises at least one computer processor and at least one computer readable medium including instructions that, when executed by the at least one computer processor, cause the chemical sensing system to perform a training process. The training process comprises accessing a training dataset including first values representing first signals output from a first chemical sensing unit of multiple chemical sensing units, and second values representing second signals output from a second chemical sensing unit of the multiple chemical sensing units, and training a set of models to relate the first values and the second values to a mutual latent representation using the training dataset.

29 Claims, 17 Drawing Sheets

(56) References Cited

U.S. PATENT DOCUMENTS

| | | | |
|---|---|---|---|
| 6,882,940 B2 | 4/2005 | Potts | |
| 7,640,116 B2 | 12/2009 | Duong et al. | |
| 7,858,720 B2 | 12/2010 | Ryan et al. | |
| 8,024,133 B2 | 9/2011 | Homer et al. | |
| 8,187,865 B2 | 5/2012 | Yun et al. | |
| 8,338,552 B2 | 12/2012 | Ryan et al. | |
| 9,080,942 B2 | 7/2015 | Zhong et al. | |
| 10,049,302 B1* | 8/2018 | Liu | G06F 17/18 |
| 10,386,379 B1 | 8/2019 | Khomami Abadi et al. | |
| 2007/0192035 A1* | 8/2007 | Schweitzer | G16C 20/20 |
| | | | 702/19 |
| 2009/0079977 A1 | 3/2009 | Lipson | |
| 2017/0206464 A1* | 7/2017 | Clayton | G06N 3/0445 |
| 2018/0082172 A1* | 3/2018 | Patel | G06N 3/0472 |
| 2018/0096232 A1 | 4/2018 | Danielsson et al. | |
| 2019/0027249 A1 | 1/2019 | Fuksenko | |
| 2019/0108421 A1* | 4/2019 | Abbott | H04N 5/23229 |
| 2019/0234973 A1 | 8/2019 | Khomami Abadi et al. | |
| 2019/0237163 A1* | 8/2019 | Wang | G06N 3/0454 |
| 2019/0244680 A1* | 8/2019 | Rolfe | G16H 50/20 |
| 2019/0294999 A1* | 9/2019 | Guttmann | G06K 9/6219 |

OTHER PUBLICATIONS

Daniel T Chang, "Latent Variable Modeling for Generative Concept Representations and Deep Generative Models", arXiv: arXiv: 1812.11856, Bibcode: 2018arXiv181211856C., Dec. 2018 (Year: 2018).*

International Search Report and Written Opinion for International Application No. PCT/IB2019/000107 dated Jun. 27, 2019.

Zhang et al., Manifold Regression Framework for Characterizing Source Zone Architecture. IEEE Transactions on Geoscience and Remote Sensing. 2016;54(1):3-17.

PCT/IB2019/00107, Jun. 27, 2019, International Search Report and Written Opinion.

PCT/IB2020/000127, Jul. 3, 2020, International Search Report and Written Opinion.

International Search Report and Written Opinion in connection with International Application No. PCT/IB2020/000127, dated Jul. 3, 2020.

* cited by examiner

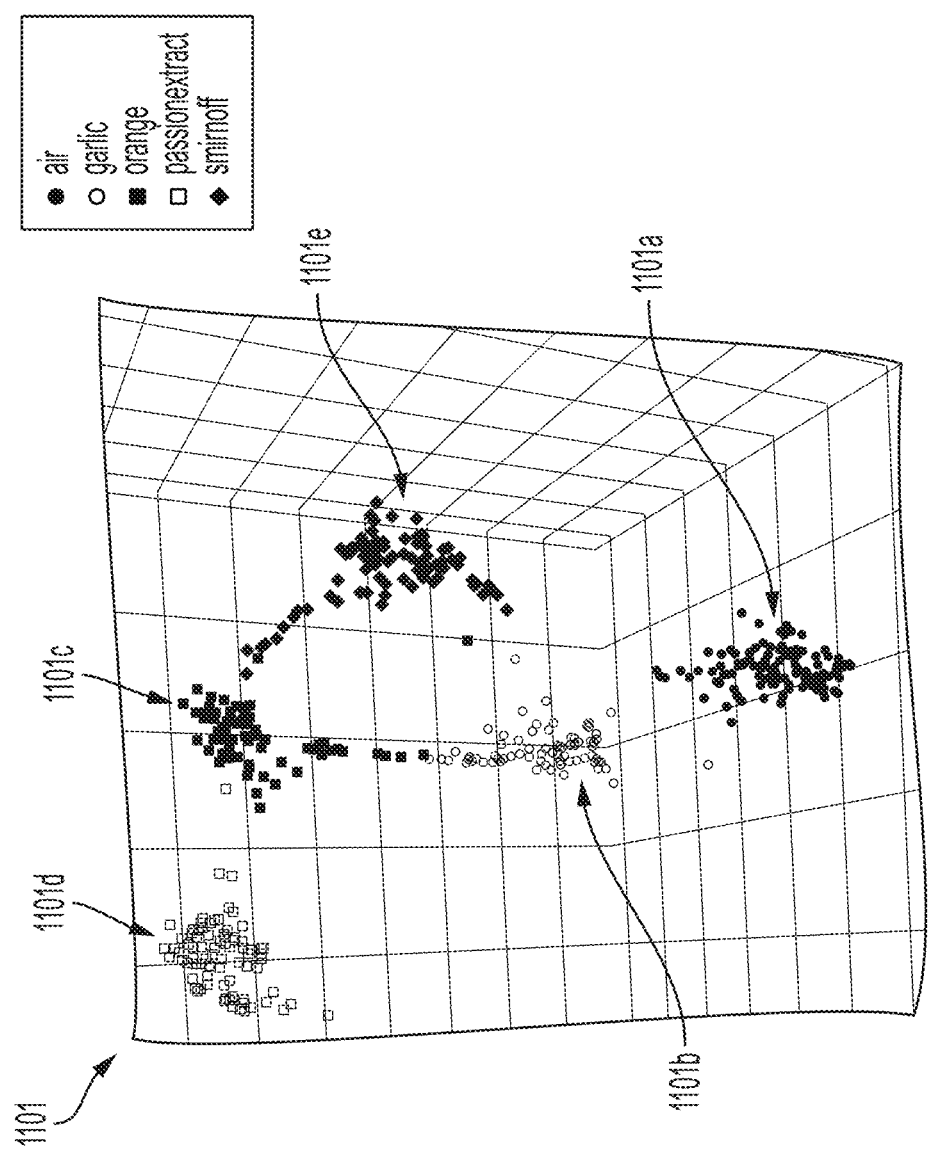

SYSTEMS AND METHODS FOR LEARNING ACROSS MULTIPLE CHEMICAL SENSING UNITS USING A MUTUAL LATENT REPRESENTATION

RELATED APPLICATIONS

This application claims priority under 35 U.S.C. § 119(e) to U.S. Provisional Application 62/809,364 entitled, "CHEMICAL SENSING SYSTEMS FOR MANY CHEMICAL SENSING SENSORS CONSIDERING WEAK SUPERVISION AND SEQUENTIAL INFORMATION," filed Feb. 22, 2019, the entire contents of which is incorporated by reference herein.

BACKGROUND

Direct and indirect interactions with chemicals in the environment can adversely affect human physical and mental health. Chemicals in the environment may include, for example, particulates and volatile organic compounds ("VOCs") generated at hospitals, chemicals emanating from food spoilage, VOCs exhaled in breath, industrial and automobile exhausts, and early indications of processes such as disease, food spoilage, and combustion.

SUMMARY

Aspects of the present application relate to a real-time, low-cost, low-power, miniature chemical sensing system capable of simultaneously sensing multiple chemicals. The system includes a component, which may be a sensor chip, that contains an array of nanocomposite sensors. These sensors are configured to produce a unique fingerprint for any given chemical or combination of chemicals. Each nanocomposite is, in general, sensitive to a particular chemical (e.g., ammonia), but is also cross-sensitive to other chemicals (e.g., acetone, carbon dioxide). Although individual sensors may lack high selectivity, an array of sensors formed from the combination of cross-sensitive polymers can generate a response pattern specific to a particular chemical combination. This approach allows for targeting a broad range of chemical analytes for identification and quantification. Additionally, this approach allows for creating large, centralized reference databases of chemical fingerprints, which can then be used to train machine-learning models capable of deconvolving the fingerprint of a complex mixture of chemicals.

According to some embodiments, a chemical sensing system is provided comprising at least one computer processor and at least one computer readable medium including instructions that, when executed by the at least one computer processor, cause the chemical sensing system to perform a training process. The training process may comprise: accessing a training dataset including first values representing first signals output from a first chemical sensing unit of multiple chemical sensing units, and second values representing second signals output from a second chemical sensing unit of the multiple chemical sensing units; and training a set of models to relate the first values and the second values to a mutual latent representation using the training dataset.

In some embodiments, training the set of models may include training one or more first models of the set of models to relate the first values representing the first signals to a first feature representation, and to relate the second values representing the second signals to a second feature representation.

In some embodiments, training the set of models may include training one or more second models of the set of models to relate the first feature representation to a first latent representation, and to relate the second feature representation to a second latent representation.

In some embodiments, training the set of models may include training one or more third models of the set of models to relate the first latent representation to the mutual latent representation, and to relate the second latent representation to the mutual latent representation.

In some embodiments, training the set of models may include training a fourth model of the set of models to generate inferences based on the mutual latent representation.

In some embodiments, training the one or more first models to relate the first values representing the first signals to the first feature representation may comprise training a first model of the one or more first models to determine a first mapping between the first values representing the first signals and the first feature representation, and training the one or more second models to relate the second values representing the second signals to the second feature representation comprises training a second model of the one or more first models to determine a second mapping between the second values representing the second signals and the second feature representation.

In some embodiments, the first model of the one or more first models and the second model of the one or more first models may be a same model and the first mapping and the second mapping may be a same mapping.

In some embodiments, training the one or more second models to relate the first feature representation to the first latent representation may comprise training a first model of the one or more second models to determine a first mapping between the first feature representation and the first latent representation, and training the one or more second models to relate the second feature representation to the second latent representation may comprise training a second model of the one or more second models to determine a second mapping between the second feature representation and the second latent representation.

In some embodiments, the first model of the one or more second models and the second model of the one or more second models may be same model, and the first mapping and the second mapping may be a same mapping.

In some embodiments, training the one or more third models to relate the first latent representation to the mutual latent representation may comprise training a first model of the one or more third models to determine a first mapping between the first latent representation and the mutual latent representation and training the one or more third models to relate the second latent representation to the mutual latent representation may comprise training a second model of the one or more third models to determine a second mapping between the second latent representation and the mutual latent representation.

In some embodiments, the first model of the one or more third models and the second model of the one or more third models may be a same model, and the first mapping and the second mapping may be a same mapping.

In some embodiments, the training process may further comprise receiving, after training the set of models, a second training dataset including third values representing third signals output from a third chemical sensing unit and training a second set of models using the second training dataset and the trained set of models.

In some embodiments, training the second set of models using the second training dataset and the trained set of models may comprise: training a fifth model to relate the third values representing the third signals to a third feature representation; training a sixth model to relate the third feature representation to a third latent representation; and training a seventh model to relate the third latent representation to the mutual latent representation.

In some embodiments, training the sixth model to relate the third feature representation to the third latent representation may comprise determining a mapping between the third feature representation and the third latent representation using the first mapping, the second mapping, or a combination thereof.

In some embodiments, training the seventh model to relate the third latent representation to the mutual latent representation may comprise determining a mapping between the third latent representation and the mutual latent representation using the first mapping, the second mapping, or a combination thereof.

In some embodiments, training the one or more first models to relate the first values representing the first signals to the first feature representation may comprise determining a sequential relationship between values of the first values; and training the one or more first models to relate the second values representing the second signals to the second feature representation may comprise training the one or more first models using the determined sequential relationship between values of the first values.

In some embodiments, training the one or more second models to relate the first feature representation to the first latent representation may comprise determining a sequential relationship between values in the first feature representation; and training the one or more second models to relate the second feature representation to the second latent representation may comprise training the one or more second models using the determined sequential relationship between values in the first feature representation.

In some embodiments, training the one or more third models to relate the first latent representation to the mutual latent representation may comprise determining a sequential relationship between values in the first latent representation; and training the one or more third models to relate the second latent representation to the mutual latent representation may comprise training the one or more third models using the determined sequential relationship between values in the first latent representation.

In some embodiments, the fourth model may be configured to generate inferences based on a sequential relationship determined between values in the mutual latent representation.

In some embodiments, training the one or more first models may comprise using a manifold learning technique, a neighborhood embedding technique, an unsupervised learning technique, or any combination thereof.

In some embodiments, the one or more second models may comprise neural network models.

In some embodiments, the neural network models may comprise feed forward neural networks, recurrent neural networks, convolutional neural networks, or any combination thereof.

In some embodiments, the one or more third models may comprise neural network models.

In some embodiments, the neural network models may comprise feed forward neural networks, recurrent neural networks, convolutional neural networks, or any combination thereof.

In some embodiments, the fourth model may comprise a feed forward neural network, a support vector machine, a recurrent neural network, or long-short-term-memory neural network.

According to some embodiments, a method of training a set of models associated with a first chemical sensing unit, using information associated with a plurality of chemical sensing units not including the first chemical sensing unit, is provided. The method may comprise: accessing the information associated with the plurality of chemical sensing units, wherein the information relates a plurality of signals output from the plurality of chemical sensing units to a mutual latent representation; accessing a training dataset including values representing signals output from the first chemical sensing unit; and training the set of models associated with the first chemical sensing unit, using the training dataset and the information associated with the plurality of chemical sensing units, wherein training the set of models comprises: (1) training a first model of the set of models to relate the values representing the signals output from the first chemical sensing unit to a feature representation; (2) training a second model of the set of models to relate the feature representation to a latent representation; and (3) training a third model to relate the latent representation to the mutual latent representation.

In some embodiments, the information associated with the plurality of chemical sensing units may comprise at least one mapping between a plurality of latent representations associated with the plurality of chemical sensing units, and the mutual latent representation.

In some embodiments, training the third model to relate the latent representation to the mutual latent representation may comprise determining a mapping between the latent representation and the mutual latent representation, using the at least one mapping between the plurality of latent representations and the mutual latent representation.

In some embodiments, the determined mapping between the latent representation and the mutual latent representation may comprise a combination of multiple mappings of the at least one mapping between the plurality of latent representations and the mutual latent representation.

In some embodiments, the information associated with the plurality of chemical sensing units may comprise at least one mapping between a plurality of feature representations associated with the plurality of chemical sensing units, and the plurality of latent representations associated with the plurality of chemical sensing units.

In some embodiments, training the second model to relate the feature representation to the latent representation may comprise determining a mapping between the feature representation and the latent representation, using the at least one mapping between the plurality of feature representations and the plurality of latent representations.

In some embodiments, determining the mapping between the feature representation and the second latent representation may comprise combining multiple mappings of the at least one mapping between the plurality of feature representations and the plurality of latent representations.

In some embodiments, training the first model may comprise using a manifold learning technique, a neighborhood embedding technique, an unsupervised learning technique, or any combination thereof.

In some embodiments, the second models may comprise a neural network model.

In some embodiments, the neural network model may comprise a feed forward neural network, a recurrent neural network, a convolutional neural network, or any combination thereof.

In some embodiments, the third model may comprise a neural network model.

In some embodiments, the neural network model may comprise a feed forward neural network, a recurrent neural network, a convolutional neural network, or any combination thereof.

According to some embodiments, a system is provided comprising at least one computer processor and at least one non-transitory computer-readable storage medium storing processor-executable instructions that, when executed by the at least one computer processor, may cause the at least one computer processor to: access signals output from a chemical sensing unit having a plurality of sensors configured to sense at least one analyte in a sample, and generate an inference regarding the at least one analyte in the sample using a set of models trained to relate the signals to mutual latent representation values in a mutual latent representation, wherein the mutual latent representation was generated based on signals output from a plurality of chemical sensing units.

In some embodiments, generating the inference regarding the at least one analyte in the sample may comprise generating feature representation values by providing the signals as input to a first model of the set of models trained to relate the received signals to a feature representation.

In some embodiments, generating the inference regarding the at least one analyte in the sample may comprise generating latent representation values by providing the feature representation values as input to a second model of the set of models trained to relate the feature representation to a latent representation.

In some embodiments, generating the inference regarding the at least one analyte in the sample may comprise generating the mutual latent representation values by providing the latent representation values as input to a third model trained to relate the latent representation to the mutual latent representation.

In some embodiments, generating the inference regarding the at least one analyte in the sample may comprise generating the inference by providing the mutual latent representation values as input to a fourth model trained to generate inferences based on the mutual latent representation.

In some embodiments, any two or more models of the set of models may be combined into a single model.

In some embodiments, the signals may be output from a plurality of chemical sensing units that output differing signals when exposed to a same analyte.

In some embodiments, the signals may be stored in the at least one non-transitory computer-readable storage medium of the system.

In some embodiments, the at least one computer processor may access the signals output from the chemical sensing unit by receiving the signals directly from the chemical sensing unit.

In some embodiments, the signals may be stored in a storage medium different from and external to the at least one non-transitory computer-readable storage medium.

In some embodiments, wherein accessing the signals may comprise receiving the signals from the storage medium.

In some embodiments, the chemical sensing unit may comprise the external storage medium.

In some embodiments, information representing at least a portion of the set of models may be stored in the at least one non-transitory computer-readable storage medium of the system.

In some embodiments, information representing at least a portion of the set of models may be stored in a storage medium different from and external to the at least one non-transitory computer-readable storage medium.

In some embodiments, the information representing at least a portion of the set of models may be received from the at least one non-transitory storage medium.

In some embodiments, the chemical sensing unit may include the at least one non-transitory storage medium.

In some embodiments, the at least one computer processor may comprise a plurality of computer processors.

According to some embodiments, a chemical sensing system may be provided comprising: (1) a plurality of chemical sensing units, each chemical sensing unit of the plurality of chemical sensing units having a plurality of sensors arranged on at least one substrate, wherein a first sensor and a second sensor of the plurality of sensors have different sensitivities to sense at least one analyte in a sample, each of the plurality of sensors being configured to output a signal in response to sensing the at least one analyte; and (2) at least one computer processor programmed to receive the signals output from the plurality of sensors for the plurality of chemical sensing units and determine a concentration of the at least one analyte in the sample by: (i) providing the received signals as input to a first model trained to relate the signals to a feature representation to generate feature representation values; (ii) providing the feature representation values as input to a second model trained to relate the feature representation to a latent representation to generate latent representation values; (iii) providing the latent representation values as input to a third model trained to relate the latent representation to a mutual latent representation to generate mutual latent representation values; and (iv) providing the mutual latent representation values as input to a fourth model trained to related the mutual latent representation to analyte concentrations to generate the concentration of the at least one analyte in the sample.

The foregoing summary is provided by way of illustration and is not intended to be limiting. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

FIGS. 11A-C depict graphic representations of exemplary latent and mutual latent spaces, according to some embodiments.

DETAILED DESCRIPTION

Figure 1A:
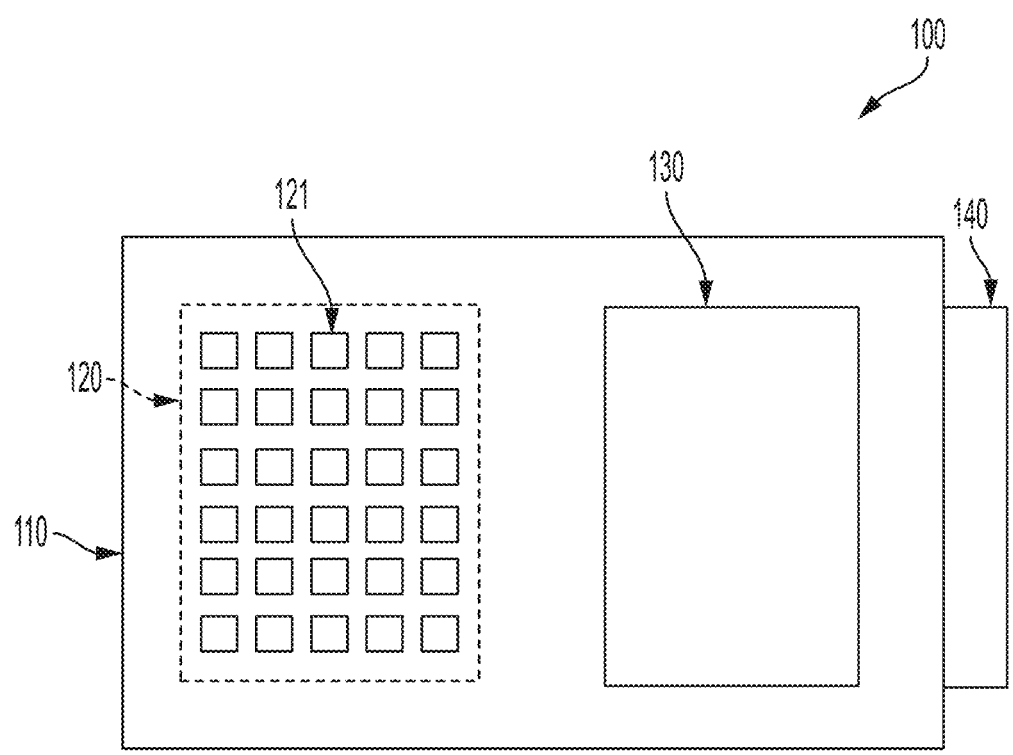
FIGS. 1A-1C depict components of an exemplary chemical sensing system.

Chemical sensors are physical devices that exhibit a measurable response to the presence of one or more chemical species. In a chemical sensor array, multiple chemical sensors are operated in the context of the same sensing application. A chemical sensing unit may include a chemical sensor array seated over a surface that will be exposed to chemical fluids. In the presence of certain target chemicals, each chemical sensor may make weak bonds with the chemical molecules, resulting in one or more changes in chemo-physical characteristics of the sensor element, that are measurable via electronic analog signals. Compared to a biological olfactory system, the chemical sensors of a chemical sensing unit may mimic neural receptors, and the behavior of the signals produced by the chemical sensing unit may be similar to the output of the firing neurons.

The inventors have recognized and appreciated that, through the biological evolution of organisms, the neural receptors within the olfactory system have developed to improve organisms' ability to survive in their environment, such as by finding food or detecting prey, finding pairs for reproduction, detecting threats like hunters, spoiled food, smoke of fire, and being aware of other factors that relate to an organism's survival and that are associated with odors. The survival instinct in each organism has resulted in the evolution of neural receptors sensitive to specific odors. For example, in humans there are approximately 400 genomes that produce different types of neural receptors that reside in the human nostril (as well as all over the body) to detect odors, smells, and chemicals in the environment. The neural receptors, once exposed to certain chemicals to which they are sensitive, make bonds with the chemicals and produce signals. Different neural receptors may respond differently to the same chemical, due to the diversity in the neural receptors, their topological distribution over the body, and the slight differences in the replication of the same type of neural receptor. As a result, the neural receptors may collectively contain information representing the chemicals present in the organism's environment.

The inventors have recognized and appreciated that it may be desirable to provide a chemical sensing system that combines information obtained from multiple chemical sensing units, in order to more fully represent the semantics (e.g., chemical characteristics) of the environment of the chemical sensing system and to thereby obtain more accurate and robust chemical sensing results. In general, some conventional chemical sensing systems lack accuracy and/or robustness due to difficulties associated with effectively combining information obtained from multiple chemical sensing units. A challenge faced by such conventional systems is that variations arising between multiple chemical sensing units may cause different chemical sensing units to have different responses (e.g., output signals) when exposed to the same semantics (e.g., the chemical concentrations within an environment of the chemical sensing system over time). These variations may be due, for example, to manufacturing differences between the sensing units and/or the decay over time of the chemical sensors within the chemical sensing units after repeatedly being exposed to chemicals.

The inventors have recognized and appreciated that some conventional chemical sensing systems fail to effectively account for variations between chemical sensing units, and therefore are unable to accurately extract information from and combine signals output by multiple chemical sensing units. As a result, some conventional systems may be unable to make accurate inferences about the corresponding semantics, or may do so only with reduced time and/or cost efficiency of the chemical sensing system compared to a chemical sensing system that takes variations in chemical sensing units into account. Accordingly, the inventors have developed techniques that provide improved chemical sensing systems capable of efficiently and intelligently combining information from multiple chemical sensing units.

Some embodiments relate to training one or more models (e.g. statistical models, machine learning models, neural network models, etc.) to map signals output by a plurality of chemical sensing units of a chemical sensing system to a common representation space that at least partially accounts for differences in signals output by the different chemical sensing units. Following training of the one or more models, new signals subsequently obtained from the chemical sensing units of the chemical sensing system may be provided as input to the trained model(s) to produce corresponding values in the common representation space. Based on these values, the chemical sensing system may generate an inference (e.g., an identification, quantification, or description) regarding the corresponding semantics (e.g., chemical characteristics) of its environment.

In general, training models, such as those described herein, may require significant quantities of training data (e.g., output signals from a number of chemical sensing units) to be able to accurately characterize the chemical composition of an environment in which a chemical sensing system is placed. However, obtaining such training data can be a time-consuming and resource-intensive process. For example, obtaining training data may require a user or manufacturer of a chemical sensing system to perform repeated experiments with the chemical sensing units. These experiments may involve exposing the chemical sensing units to a variety of semantics, which may include a wide range of application-specific semantics, and recording the corresponding output signals from the chemical sensing units. In some instances, it may be desirable to train the model(s) associated with the chemical sensing system using a smaller training data set, thereby reducing the time and effort associated with training.

Some embodiments relate to techniques for reducing the amount of training data needed to integrate an additional chemical sensing unit into an existing chemical sensing system. These techniques may be referred to herein as "semi-supervised training" or "training with weak supervision." As described herein, these techniques may involve using information about previously-trained model(s) associated with the existing chemical sensing system to provide partial supervision of a training process for the additional chemical sensing unit. In particular, as part of training one or more additional models associated with the additional chemical sensing unit, a reduced quantity of training data may be utilized in combination with information about the previously-trained models, such that the additional model(s) attain an acceptable accuracy (e.g., an accuracy above a certain threshold, such as 80% accuracy). For instances, only a small fraction of the training data that would be required to train the additional model(s) without the information about the previously-trained models (e.g., less than 10% of the training data, such as 5% or 2% of the training data) may be used to obtain a desired model accuracy.

A chemical sensing unit designed in accordance with some embodiments may operate in a manner akin to olfaction in biological systems. To detect smells of interest and the smell strength in an environment, each individual chemical sensor of the chemical sensing unit may be designed to respond to one or more functional chemistry groups of interest, corresponding to the smells of interest. The smells of interest may be selected, for example, as part of a particular application for which only certain smells may be of relevance (e.g., detecting smoke, rotting food, or other phenomena associated with certain odors). In general, the environment of a chemical sensing system may be a volume, referred to herein as a headspace, in which the chemical sensing system resides.

A chemical sensor can be operated in an environment that includes one or more chemical species. At least one of the chemical species in the environment may be present in a fluid form (e.g., in a liquid phase and/or a gas phase). A chemical sensor may be sensitive to the presence of some molecules at a variety of concentrations, but may not be sensitive to others. A chemo-physical response of a sensor to various chemical species may take the form of signals output at measurable levels. The concentration of the chemical species in the environment may be quantified as a scalar value in conjunction with a chosen unit of measurement. For example, the concentration of gaseous methane in air can be quantified in terms of molar concentration.

A sensor can be configured to sense a concentration of one or more relevant chemical species (referred to herein as analytes) in the environment. The concentration of analytes in the environment is referred to herein as the composition of the environment. For example, a carbon monoxide detector can be configured to sense a concentration of carbon monoxide present in an environment also including other chemical species (e.g., oxygen and nitrogen). When a sensor array is configured to detect M analytes, a unit of measurement defines an M-dimensional vector space isomorphic to $R^M$. The elements in the vector space uniquely describe a composition of the environment. The composition of the environment as measured by a sensor may depend on a location of the sensor and may vary over time.

Figure 1B:
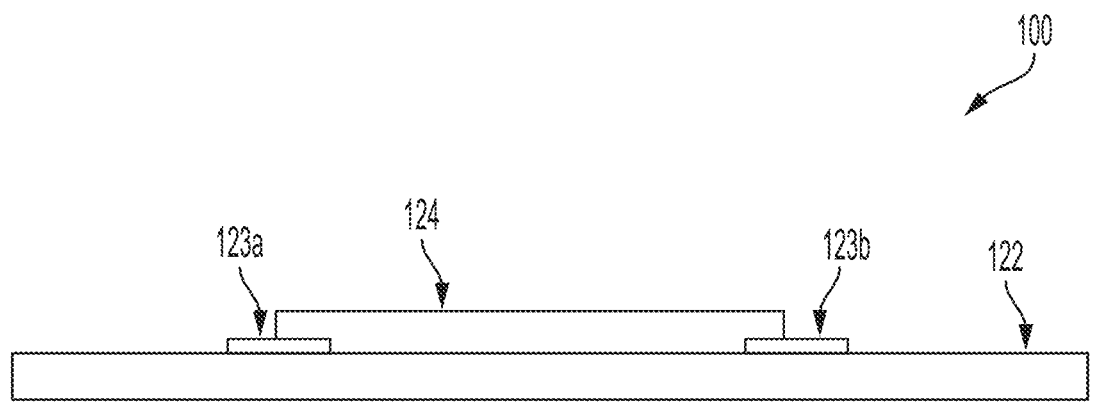

FIG. 1A and FIG. 1B depict views of an exemplary chemical sensing unit 100. Chemical sensing unit 100 includes a sensor array 120. Individual sensor outputs from a plurality of sensors in the array may exhibit incomplete information about the chemical species in the environment in which the chemical sensing unit is placed. For example, each sensor output may exhibit a dependence on multiple, time varying extraneous variables (e.g., temperature, humidity, etc.) that are not well specified based on the output of that sensor alone. By including multiple sensors in an array, the chemical sensing unit may be configured to estimate the chemical composition of an environment using multiple output signals generated by the multiple sensors in the array. As described in more detail below, some embodiments process the output from multiple sensors in an array using an inferential model to generate an estimate of a concentration of one or more chemical species in the environment.

Chemical sensing unit 100 includes a base 110 configured to support a sensor array 120. Base 110 may be implemented using any suitable substrate including, but not limited to, a circuit board. The sensor array 120 includes a plurality of sensors (e.g., sensor 121). The sensors may be arranged in rows and columns, as shown, or the sensors may be arranged in another arrangement (e.g., concentric circles, staggered rows, etc.). The described location and orientation of the sensors on chemical sensing unit 100 are not intended to be limiting.

Chemical sensing unit 100 includes a controller 130. In some embodiments, controller 130 is configured to provide power to the plurality of sensors. In some embodiments, controller 130 is configured to acquire signals from the plurality of sensors. For example, each of the sensors may include, or be a part of, a Wheatstone bridge or another circuit configured to measure changes in resistance. Controller 130 may be configured to provide power for the sensors and/or acquire signals from the sensors corresponding to changes in resistance measured by the sensors. In some embodiments, controller 130 is further configured to provide one or more of signal conditioning, signal processing, and signal communication. For example, controller 130 may be configured to filter and amplify signals received from the sensors. In some embodiments, controller 130 is further configured to perform at least some of the mapping operations described in more detail below. For example, controller 130 may be configured to implement one or more models relating the signals output by the sensors to a latent representation, or to an output representation having one or more axes corresponding to relevant analytes. In some embodiments, controller 130 includes at least one storage device (e.g., a memory) configured to store parameters that define one or more of the mapping operations, described in more detail below.

Chemical sensing unit 100 includes a communications component 140, which can include hardware and/or software configured to enable chemical sensing unit 100 to communicate with other elements of the chemical sensing unit (or other devices). For example, communications component 140 may include a network controller configured to provide local area network connectivity, a port controller configured to provide parallel port and/or serial port connectivity, and/or a wireless controller configured to provide WIFI, BLUETOOTH, ZIGBEE or similar connectivity.

In accordance with some embodiments, a sensor (e.g., sensor 121) includes a substrate 122 and one or more electrodes (e.g., electrodes 123a and 123b) disposed on substrate 122. In one implementation of sensor 121, a conductive thin film 124 is disposed on and between electrodes 123a and electrodes 123b as shown. For example, thin film 124 can include conductive nanoparticles. In some embodiments, thin film 124 is chemically sensitive. For example, thin film 124 may undergo a physical change (e.g., swelling, contracting, and/or a change in composition or state) upon exposure to an analyte. The physical change in the thin film 124 may result in a change in resistance between electrode 123a and electrode 123b. Controller 130 may be configured to monitor the resistance between electrode 123a and electrode 123b, resulting in an output signal from the sensor that is detectable by controller 130. The output signal may include semantic information concerning one or more analytes introduced to the sensor.

In some embodiments, one or more of the sensors in sensor array 120 are configured with differing sensitivities to different analytes. For example, thin films for different sensors in the array may be configured to provide different degrees of physical change in response to exposure to the same analyte. As an additional example, a thin film for a sensor can be configured to provide different degrees of physical change in response to exposure to different analytes. Accordingly, in some embodiments, the output signals from different sensors in the array may differ in the presence of the same analyte and/or the output signal from the same sensor may differ in the presence of different analytes in the environment. These differences may include, but are not limited to, differences in amplitude and/or temporal characteristics of the output signal.

Figure 1C:
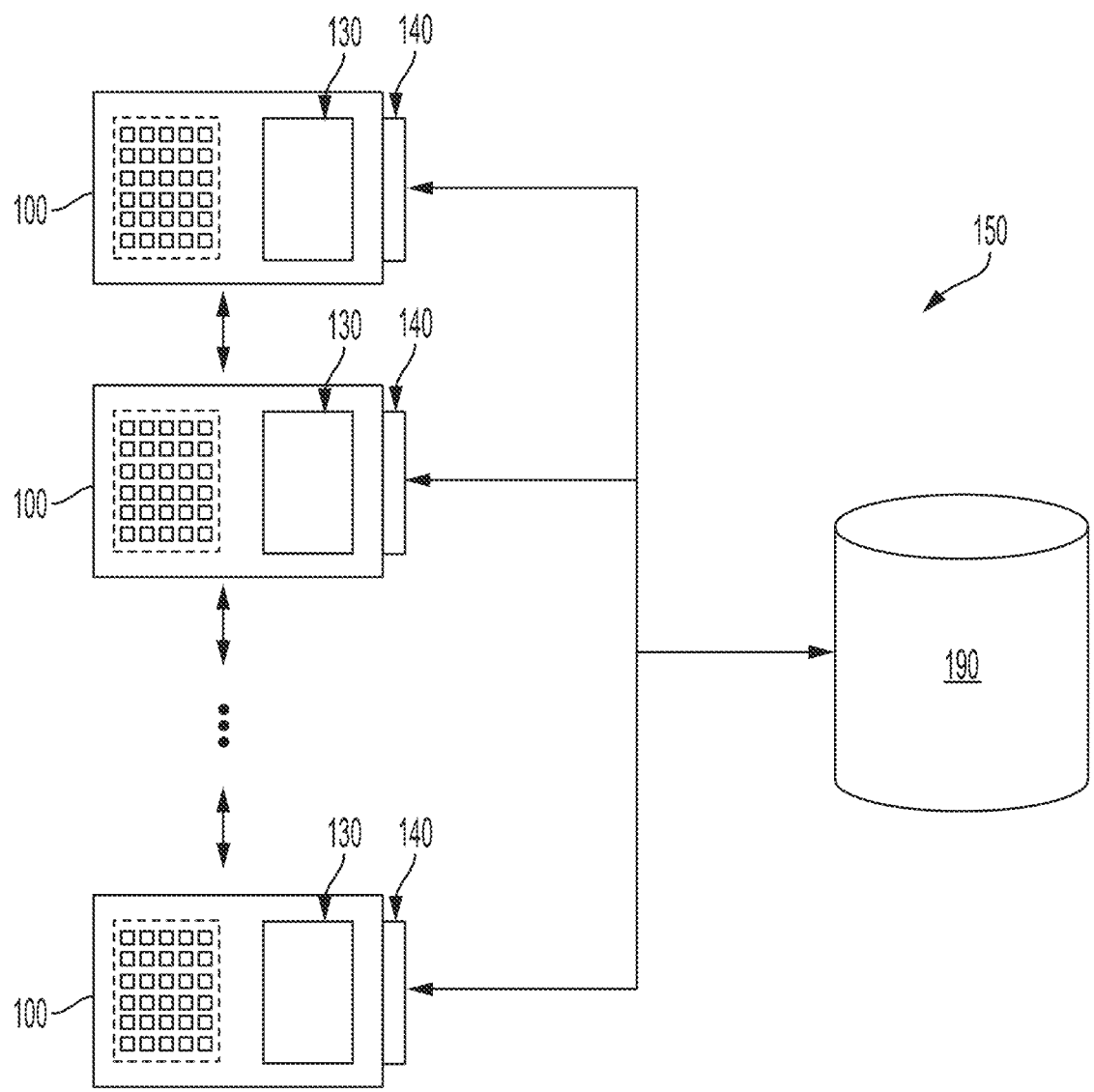

FIG. 1C depicts an exemplary chemical sensing system 150, which may include chemical sensing units 100 and, optionally, an external storage medium 190. Each of the chemical sensing units 100 may be designed in the manner described herein at least with respect to FIGS. 1A-B. As depicted in the figure, the chemical sensing units 100 of chemical sensing system 150 may be capable of communicating with one another, such as by using the communications component 140 included in each chemical sensing unit, or any other suitable channel of communication. This communication channel may be utilized to share information such as training data, model information, or output signals between the chemical sensing units 100. For a given chemical sensing unit 100, the shared information may be stored, for example, on a storage device associated with the controller 130 of the chemical sensing unit or on external storage medium 190.

As shown in FIG. 1C, external storage medium 190 may be accessible by the chemical sensing units 100 via their communications components 140. The external storage medium 190 need not be a single storage device, but may be distributed over a number of devices, such as in a cloud storage configuration. In some cases, one or more of the chemical sensing units 100 may store information such as training data, model information, or output signals on the external storage medium 190. One or more of the chemical sensing units 100 may also access information from the external storage medium 190, not limited to information stored by the chemical sensing units on the external storage medium, including training data, model information, output signals, or other information.

Figure 2A:
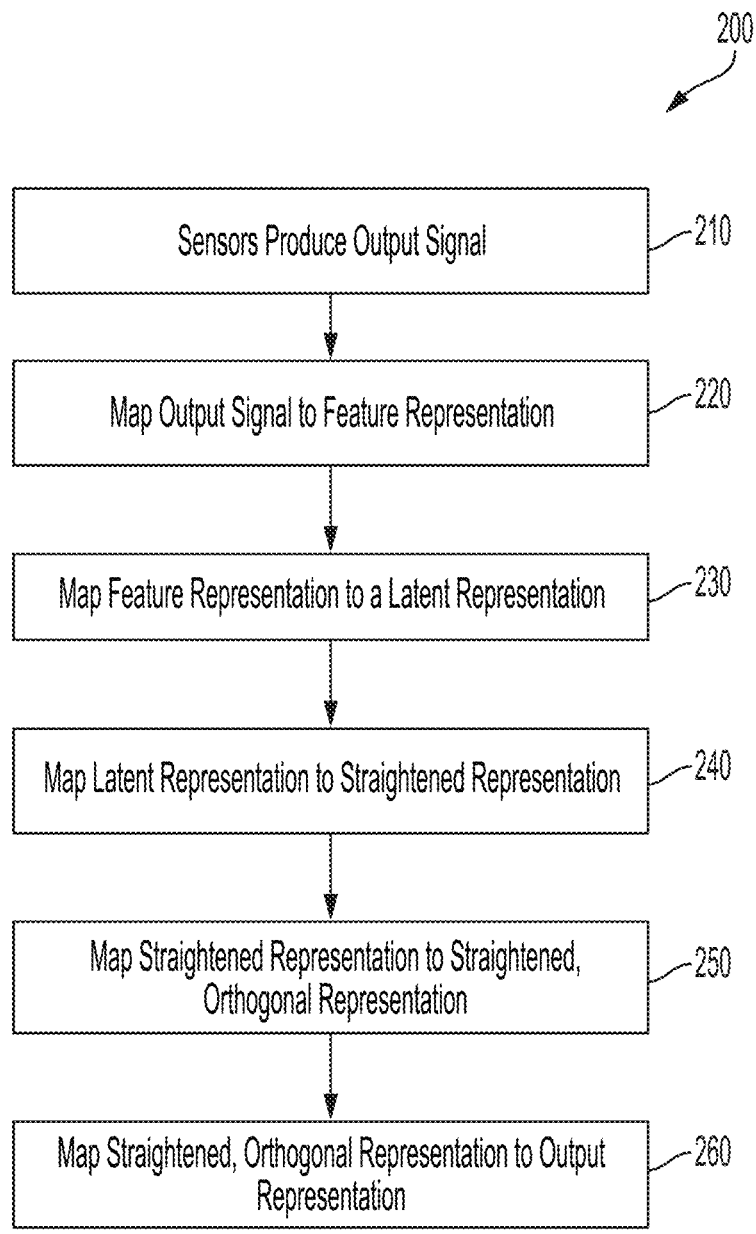
FIG. 2A depicts an exemplary sequence of mappings from signals output by sensors of a single chemical sensing unit to an output representation having bases corresponding to relevant analytes.

Similar to neural receptors, which may produce signals that undergo further processing in the central nervous system, chemical sensors included in some embodiments may produce signals, at least some of which are subsequently transformed via one or more functions. FIG. 2A depicts an exemplary process 200 of mapping signals output by sensors (e.g., the sensors of a chemical sensing unit 100) to an output representation having bases corresponding to relevant analytes (e.g., an M-dimensional vector space V, having elements $\vec{v}$, as described herein). Note that the process 200 of FIG. 2A includes steps which need not be performed in all embodiments. For example, in some embodiments, the process 200 may end at block 230, or at any other step in process 200, and may thereafter proceed with a process as described herein at least with respect to FIGS. 3 and 4.

Figure 2B:
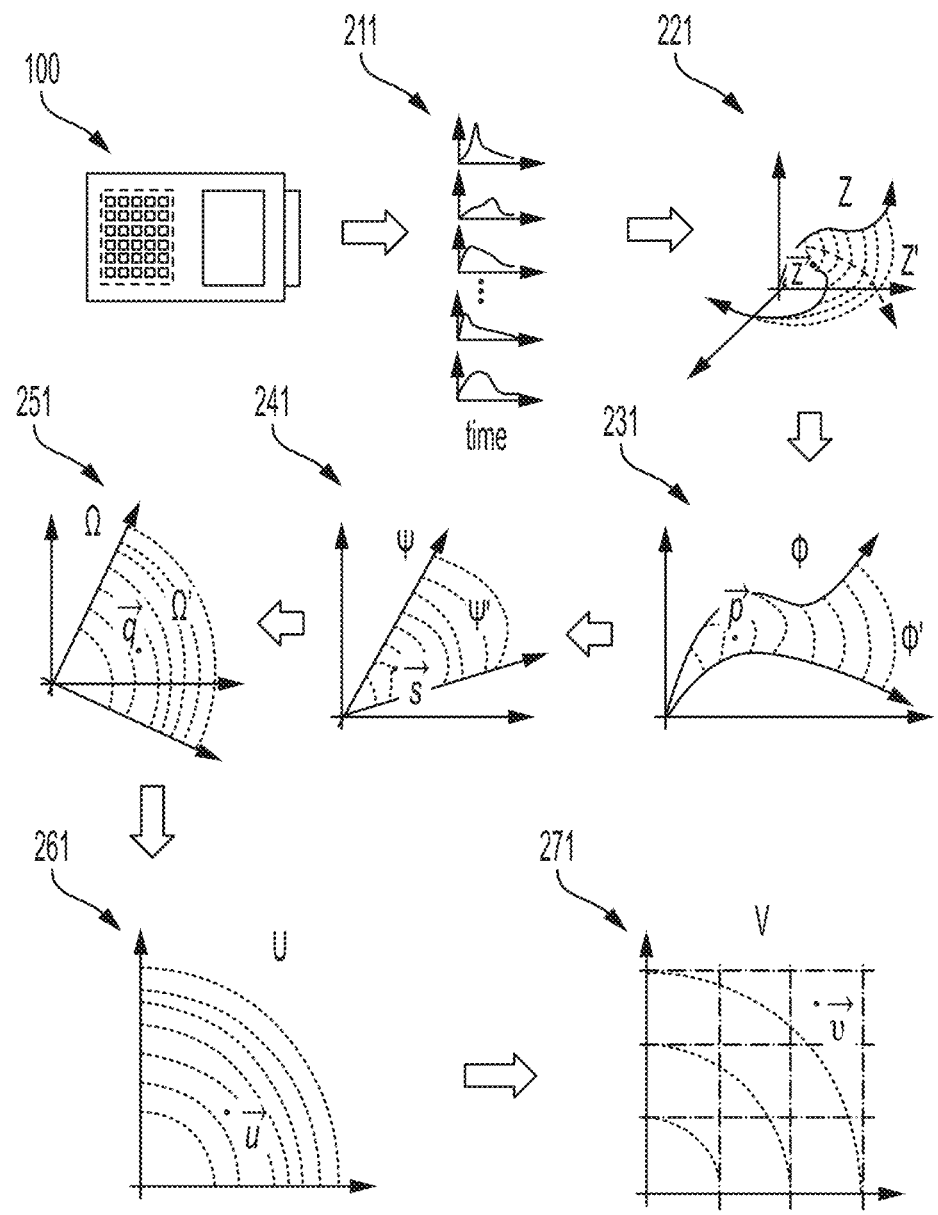
FIG. 2B depicts a sequence of exemplary representations corresponding to the mappings of FIG. 2A.

FIG. 2B depicts a sequence of exemplary representations (also referred to herein as models or sub-models) corresponding to the mappings of FIG. 2A. As discussed with respect to FIG. 2A, not all the representations depicted in FIG. 2B need be used in every embodiment. Instead, in some embodiments, only some of the depicted representations may be utilized (e.g., feature representation 221 and latent representation 231) and, thereafter, alternative representations and maps may be used, such as those described herein at least with respect to FIGS. 3 and 4.

Returning to FIG. 2A, the exemplary process 200 begins at operation 210, where chemical sensors produce output signals. In general, the process 200 can operate on input data (e.g., datasets, streaming data, files, or the like) in a variety of formats, such as divided into semantically separate partitions corresponding to different environmental and operational contexts. For example, the input data may be divided into multiple datasets, data streams, files, etc. corresponding to different sensors, times, contexts, environments, or the like. Such partitions may contain multiple input data entries, one input data entry, or no input data entries. Under such partitioning, the datasets and data streams may be viewed as composites of the individual semantic partitions, and the analyses applied to the datasets and data streams may be equivalently applied to semantic partitions and vice-versa.

As described herein, the input data may include output signals obtained from sensors (e.g., raw data output from the sensors) and/or data derived from the signals output from the sensors (e.g., one or more features extracted from the output signals). In some aspects, the output signals obtained from the sensors may be filtered to reduce noise in the output signals. Any suitable filtering technique may be used depending on the nature of the sensor response and the noise present in the output signals. Unless otherwise specified, the output signals described herein may be either filtered output signals or non-filtered output signals. In some embodiments, the input data includes time values. For example, the input data may include timestamps corresponding to output signal values. In some embodiments, time values may be implicitly determined from the data. For example, the input data may include an initial timestamp and a sampling frequency such that time values for input data following the initial timestamp may be determined based on the initial timestamp and the sampling frequency.

In some embodiments, the input data can include concentration information corresponding to the output signals. When the input data lacks concentration information for all of the relevant analytes, the input data is referred to herein as "unlabeled data." When the input data lacks concentration information for some of the relevant analytes, the input data is referred to herein "partially labeled data." When the input data includes concentration information for all of the relevant analytes, the input data is referred to herein as "labeled data." In some embodiments, the input data includes contextual information. The contextual information may include, for example, information about the environment of the device such as the temperature of the environment, the application the system is employed in, explicit information about the presence or absence of irrelevant analytes, or other contextual information relating to the operation of the sensor array.

In some embodiments, process 200 is implemented by sequentially applying one or more models to the data. The one or more models may include parameters and hyperparameters stored in a memory component of the chemical sensing system. In some embodiments, the parameters are learned using machine learning techniques, examples of which are described in more detail below. A chemical sensing system configured to apply the sequence of one or more models according to the learned parameters and hyperparameters to output signals may infer a chemical composition of an environment from the output signals.

A sequence of models that collectively map the input data to the output representation (e.g., the vector space V) may be generated in place of a single model that performs the same function. Using a sequence of models may improve the flexibility of the chemical sensing system. Furthermore, the effect of each individual model may be more easily reviewed and/or interpreted when using a sequence of models that collectively map the input data to the output representation, allowing for convenient adjustment or debugging of individual models.

In some embodiments, the sequence of models may include a first model that relates the output signals to an intermediate representation (e.g., a feature representation, latent representation, or straightened orthogonal representation, as described herein) and a second model that relates the intermediate representation to the output representation. Different versions of the first model may be specific to different implementations or instances of chemical sensing unit 100. Similarly, different versions of the second model may relate the intermediate representation to different output representations. Depending on the chemical sensing system and the desired output representation, an appropriate version of the first model may be used together with the appropriate version of the second model. The two models may be generated separately (e.g., at different times or locations, or by different devices), or applied separately.

As one example, a first chemical sensing system can apply the first model to the output signals to generate the intermediate representation. A second chemical sensing system can subsequently apply the second model to the intermediate representation to generate the output representation. In some embodiments, the first model can be specific to the first device. Thus, a first device-specific model can be trained to map input data acquired by the first device to the intermediate representation. The first device-specific model can subsequently be used to specify initial parameters for training additional device-specific models. For example, when training a second device-specific model for a second device, at least some of the parameters of the second device-specific model can be initialized to at least some of the parameters of the first device-specific model. In some embodiments, the second model can be trained independent of any particular device. For example, when the second model is implemented as a device-independent model, it can be trained to map input data from intermediate representations generated by one or more device-specific models to the output representation.

In some embodiments, one or both of first and second models includes at least two sub-models, each of which divides the mapping for a model into multiple sub-mappings which may undergo a separate learning process. For example, in some embodiments, the second model is divided into a first sub-model relating the feature representation output from the first model to a latent representation, a second sub-model relating a latent representation to a straightened orthogonal representation, and a third sub-model relating a straightened orthogonal representation to the output representation.

The composition and training of the models and/or sub-models used in accordance with some embodiments, are described in more detail below. In some embodiments, one or more of the models or sub-models are trained using parametric techniques, such as support vector machines, random forests, or deep neural networks. In other embodiments, one or more of the models or sub-models are trained using non-parametric techniques, such as t-distributed stochastic neighbor embedding (t-SNE), uniform manifold approximation and projection (UMAP), or k-nearest neighbors techniques (k-NN).

For convenience, FIGS. 2A and 2B are described with regard to tuples of the form $\{D(t_i)=(t_i, C(t_i), \vec{x}(t_i), \vec{a}(t_i))\}$, where $t_i$ is a unique timestamp, $\vec{x}(t)=\langle(x_1(t), \ldots, x_N(t)\rangle$ is the response of a sensor array including N sensors at time $t_i$, and $\vec{a}(t_i)$ may be the corresponding vector of concentrations of relevant analytes. As described above, $\vec{x}(t)$ may represent a filtered version of the output signals from the sensors to reduce noise in the output signals. When information about the concentration of a relevant analyte is not available, the corresponding elements of $\vec{a}(t_i)$ may include an element (a "null element") indicating the unavailability of such information (e.g., a default value, a NaN, or the like). For example, when no information about the concentration of relevant analytes is available, $\vec{a}(t_i)$ may be a vector of null elements. As used herein, a data entry $D(t_i)$ is referred to as "unlabeled" when all elements of $\vec{a}(t_i)$ are null elements, partially labelled when some but not all elements of $\vec{a}(t_i)$ are null elements, and $D(t_i)$ is referred to as "labelled" when none of the elements of $\vec{a}(t_i)$ are null elements. $C(t_i)$ may include a vector of contextual information, such as the contextual information described above. However, the disclosed embodiments are not limited to tuples of the form $\{D(t_i)=(t_i, C(t_i), \vec{x}(t_i), \vec{a}(t_i))\}$.

In operation 210, chemical sensors (e.g., sensors in sensor array 120) of a sensing device (e.g., chemical sensing unit 100) may transduce a chemical signal 3 dependent on the composition of the environment into electrical output signals $\vec{x}(t)$ (e.g., from chemical sensing unit 100 to output signals 211, as depicted in FIG. 2B). In some embodiments, the values of output signals 211 may reflect changes in the composition of the environment over time. In some embodiments, these output signals may include transient changes in value in response to a change in the composition of the environment. For example, a baseline value prior to the change in the composition of the environment may be approximately the same as a steady-state value reached after the change in the composition of the environment. In various embodiments, these output signals may reach a new steady-state value dependent on the changed composition of the environment.

According to some embodiments, the chemical sensors produce signals that may be transformed via one or more functions into tuples of numbers that provide a feature representation of the composition of the environment. Such a feature representation may be considered a numeric representation of the odor semantics associated with certain mixtures of chemicals. In some cases, odor semantics may involve changes of odors in a sequence; for example, the odor of a food recipe given a sequence of the odors produced during the cooking process. In accordance with the design and development of chemical sensors, a feature representation may contain information that identifies and/or quantifies the smells in the environment of a chemical sensing unit. As described herein, a feature representation may be produced in order to interpret the chemical composition of the gasses in the environment of the chemical sensing unit.

In operation 220, the output signals are applied to a model that relates output signals to a feature representation (e.g., a mapping from output signals 211 to feature representation 221, as depicted in FIG. 2B) to generate feature vectors corresponding to the output signals. In this manner, the model may de-convolve relevant information from the output signals. The relationship established by the model can be expressed, for an output signal $x_i(t)$, as a map to a feature representation, $\zeta_i: \mathbb{R}^{T_i} \to \mathbb{R}^{K_i}$, where $T_i$ denotes some (possibly infinitely large) number of samples that span some time interval $[t_i, t_{T_i}]$, and $K_i$ denotes a number of features extracted from the output signal. Such a map produces a feature vector, $\vec{z}_j = \zeta_i(x_i[t_i, t_{T_i}]))$, where $\vec{z}_j \in \mathbb{R}^{K_i}$. As discussed herein, i may be expressed as a parametric function of some parameter set $\theta_i$: $\vec{z}_j = \zeta_i(x_i([t_1, t_{T_i}]); \theta_i)$. Values for these parameters may be estimated using, for example, machine learning techniques such as feedforward neural networks and Gaussian processes.

In some embodiments, the number of maps $\zeta_i$ may not equal the number of output signals $x_i(t)$. For example, features may not be extracted from some output signals (resulting in fewer maps), or features may be extracted from combinations of output signals in addition to individual output signals (resulting in additional maps). In general, when the number of output signals is N, the number of maps $\zeta_i$ will be equal to N'. The result of applying $\zeta = \{\zeta_1, \ldots, \zeta_{N'}\}$ to $\vec{x}(t)$ may be expressed as a composite feature vector $\vec{z} = \langle z_1, \ldots, z_{N'} \rangle$, where $\vec{z} \in \mathbb{R} \in \mathbb{R}^K$, and $K = \Sigma_i K_i$ is the collection of features extracted from all maps comprising $\zeta$. As used herein, such a composite feature vector is referred to as a feature vector. For $\vec{z}$ as defined above, let the span of all possible feature vectors $\vec{z}$ be denoted as the feature space Z, where $Z \subseteq \mathbb{R}^K$.

In some embodiments, N may be a large number, and K may be larger than N. As such, numerical methods applied in Z may suffer from the curse of dimensionality. Furthermore, a change in concentration $\Delta\vec{v}$ may yield a non-linear change $\Delta\vec{z}$ in the feature vector, which may, in some cases, preclude the use of linear dimensionality reduction techniques.

In some embodiments, properties of the feature space Z may be used to associate feature vectors with analytes, without relying on vectors of concentrations of relevant analytes (e.g., without relying on $\vec{a}(t_i)$). These associations may be used to train models that implement mappings imposing straightness and orthogonality conditions on the data. For example, an association can be created between feature vectors corresponding to varying concentrations of the same analyte. A model can be generated, using this association, that implements a mapping to a representation in which points corresponding to the feature vectors are aligned along a single vector. As an additional example, a first association can be created between first feature vectors corresponding to varying concentrations of a first analyte and a second association can be created between second feature vectors corresponding to varying concentrations of a second analyte. A model can be generated, using the first and second associations, that implements a mapping to a representation in which first points corresponding to the first feature vectors are aligned along a first vector, second points corresponding to the second feature vectors are aligned along a second vector, and the first vector and second vector are orthogonal.

In some embodiments, an iterative process is used to identify feature vectors corresponding to varying concentrations of a single analyte. This process can be performed automatically (e.g., without user direction or input). This approach assumes that feature vectors corresponding to varying concentrations of a single analyte are on the outside, or hull, of manifold Z'. Points in Z' corresponding to combinations of two or more analytes may lie between these exterior points, either on the hull of manifold Z' or in the interior of manifold Z'. A sequence of samples including a fixed concentration of a first analyte and decreasing concentrations of a second analyte approach a location in Z' corresponding to the fixed concentration of a first analyte along a first trajectory. A sequence of samples including the fixed concentration of the first analyte and decreasing concentrations of a third analyte approach the location in Z' corresponding to the fixed concentration of the first analyte along a second trajectory, distinct from the first trajectory. Thus, points corresponding to varying concentrations of a single analyte can be identified as points on the hull of manifold Z' where trajectories defined by neighboring points change (e.g., locations with local gradient changes). The following iterative process may be used to identify such points.

As a first step, a space D is initialized to equal space Z and includes all of the points in space Z. A point $z_1$ in D is selected. Another point $z_2$ in a neighborhood of $z_1$ is selected and a vector $\overrightarrow{z_1 z_2}$ is created. A sequence of points is then identified, each point in the sequence in a neighborhood of the preceding point in the sequence satisfying a directionality criterion with respect to $\overrightarrow{z_1 z_2}$. Satisfaction of this directionality criterion may indicate that a point is sufficiently aligned with the vector $\overrightarrow{z_1 z_2}$. In some embodiments, the directionality criterion may depend on a vector between the preceding point in the sequence and the current point in the sequence. For example, the directionality criterion may depend on a cosine value of the angle between $\overrightarrow{z_1 z_2}$ and the vector. When the cosine value is less than a threshold, the directionality criterion may not be satisfied. For example, a first point $z_3$ in the sequence may be in a neighborhood of $z_2$ and may satisfy the directionality criterion when a cosine value of the angle between $\overrightarrow{z_1 z_2}$ and $\overrightarrow{z_1 z_3}$ is greater than a threshold. In various embodiments, the directionality criterion may depend on a distance from the next point in the sequence to a projection of the vector $\overrightarrow{z_1 z_2}$. The sequence may end when no further point can be identified along this direction. Additional sequences can be generated in this fashion for all points $z_1$ in Z and $z_2$ in the neighborhood of $z_1$. The set of final points E for all of the sequences may then define a boundary space in D. The space D can be updated to include only the boundary points E. The process of identifying boundary points can then be repeated to generate a new set of final points E.

This process can be repeated until E comprises a set of one-dimensional manifolds that cross an origin corresponding to an absence of a sensor response. Each of these one-dimensional manifolds comprises feature vectors corresponding to pure chemicals or base analytes. By applying this process, feature vectors can be associated with one-dimensional manifolds correspondent to the base analytes. This association can then be used to perform unsupervised learning in operations 241 and 251, without relying on labels for the samples. In semi-supervised techniques, partial availability of labels indicating concentrations associated with feature vectors can help validate the formation of each map and space by comparing a label for a sample with a position corresponding to the sample in each space. Partial labels can also be used to label an axis corresponding to base analytes. For example, when a sample lies on or near an axis and a label for the sample indicates concentrations of analytes, the axis can be labeled as corresponding to the analyte having the greatest concentration.

In some embodiments, $\vec{x}(t)$ may be continuous with respect to changes in $\vec{v}(t)$. Mapping may be selected so as to preserve the continuity of $\Delta \vec{z}(t)$ with respect to $\Delta \vec{v}(t)$. When the output signal $\vec{x}(t)$ is unique for each chemical composition of the environment $\vec{v}(t)$, and $\zeta$ is selected to preserve uniqueness of $\vec{z}$ with respect to $\vec{v}$, then there exists a one-to-one mapping $H^{-1}$ between the exemplary output representation V and Z' where the image V defines a continuous manifold $Z' \subseteq Z$ as depicted in FIG. 2B.

When exemplary output representation V and Z' are open sets, the one-to-one mapping $H^{-1}$ is a homeomorphism. By definition, a homeomorphism H then exists between Z' and V. In such instances, Z' comprises a manifold of dimension M embedded in Z (as depicted in feature space 221 of FIG. 2B). Furthermore, each dimension of V maps to a one-dimensional, potentially non-linear manifold embedded in Z'. The mapping $\Omega$ from Z' and V may thus be decomposed into sub-mappings. As described above, sub-models may implement these sub-mappings. Such sub-models may be easier to generate than a model that implements H, and may provide additional flexibility to the chemical sensing system.

In operation 230, the feature vectors generated in operation 220 can be applied to a first sub-model that relates the feature representation Z to a latent representation $\Phi$ (e.g., from feature representation 221 to latent representation 231, as depicted in FIG. 2B) to generate latent value vectors corresponding to the feature vectors. In some embodiments, the latent representation $\Phi$ can be an inner product space. The latent representation $\Phi$ can be of the same dimension as the manifold Z'. As a non-limiting example, when Z' is a plane embedded in Z, then the latent representation $\Phi$ may be a two-dimensional space (e.g., latent representation 231, as depicted in FIG. 2B). The first sub-model may implement a mapping $\Phi: Z \to \Phi$. Such a map may produce a latent value vector $\vec{p} = \varphi(\vec{z})$, where $\vec{p} \in \mathbb{R}^{dim(z')}$. In some embodiments, when Z' is not embedded in Z, $\varphi$ may reduce to the identity function. As discussed herein, $\varphi$ may be expressed as a parametric function of some parameter set $\Lambda$: $\vec{p} = \varphi(\vec{z}; \Lambda)$. Values for parameter set $\Lambda$ may be estimated using machine learning techniques such as feedforward neural networks and Gaussian processes. In some embodiments, the mapping $\varphi: Z \to \Phi$ fulfills the following conditions: $\varphi$ is a continuous mapping between Z' and $\Phi$, $\varphi$ is bijective from Z' to $\Phi$, $\varphi^{-1}$ is a continuous mapping between $\Phi$ and Z', and $\varphi^{-1}$ is bijective from $\Phi$ and Z'. The above conditions may follow from the homeomorphism between Z' and $\Phi$.

In operations 240 and 250, the latent value vectors generated in operation 230 can be applied to a second sub-model that relates the latent representation $\Phi$ to a straightened, orthogonalized representation $\Omega$. In some embodiments, this second sub-model includes two component models. As described above, multiple component models may provide more flexibility and be more easily interpreted than a single model providing the same functionality.

In operation 240, the latent value vectors generated in operation 230 can be applied to the first component model to generate aligned vectors corresponding to the latent value vectors (e.g., from latent representation 231 to straightened representation 241, as depicted in FIG. 2B). The first component model may relate latent representation $\Phi$ to straightened representation $\Psi$. In latent representation $\Phi$, samples including varying concentrations of a single analyte may be described by a non-linear, one-dimensional manifold. The first component model may implement a mapping $\psi: \Phi \to \Psi$ that maps each such manifold to a straightened non-linear, one-dimensional manifold in $\Psi$. For example, two differing concentrations of the same analyte (e.g., $\vec{v}_2 = c\vec{v}_1$, $\vec{v}_1, \vec{v}_2 \in V$, $c \in \mathbb{R}$) may map to two latent value vectors (e.g., $\vec{p}_1, \vec{p}_2 \in \Phi$). Mapping $\psi$ may map $\vec{p}_1$ and $\vec{p}_2$ to $\vec{s}_1, \vec{s}_2 \in \Psi$ such that an angle between $\vec{s}_1$ and $\vec{s}_2$ is minimized. For example, $\psi$ may be determined such that cosine distance $d(\vec{s}_1, \vec{s}_2)$ is maximized. When the manifolds in $\Phi$ are already straight, $\psi$ may reduce to the identity function. As discussed herein, $\psi$ may be expressed as a parametric function of some parameter set $\Sigma$: $\vec{s} = \psi(\vec{p}; \Sigma)$. Values for parameter set $\Sigma$ may be estimated using machine learning techniques, such as feedforward neural networks and Gaussian processes. In some embodiments, the mapping $\psi: \Phi \to \Psi$ fulfills the following conditions: $\psi$ is a continuous mapping between $\Phi$ and $\Psi$, $\psi$ is bijective from $\Phi$ to $\Psi$, $\psi^{-1}$ is a continuous mapping between $\Psi$ and $\Phi$, and $\psi^{-1}$ is bijective from $\Psi$ to $\Phi$. The above conditions may follow from the homeomorphism between $\Psi$ and $\Phi$. Furthermore, function $\psi$ may reduce the impact of noisy data, as $\psi$ may align latent value vectors in $\Phi$ corresponding to noisy measurements of the same analyte along the same direction in $\Psi$.

In operation 250, the latent value vectors generated in operation 230 can be applied to the second component model to generate independent vectors corresponding to the aligned vectors (e.g., from straightened representation 241 to orthogonal, straightened representation 251, as depicted in FIG. 2B). The second component model may relate straightened representation $\Psi$ to straightened, orthogonal representation $\Omega$. In straightened representation $\Psi$, varying concentrations of the same analyte may map to a straightened, non-linear, one-dimensional manifold (e.g., straightened representation 241, as depicted in FIG. 2B). The second component model may implement a mapping $\omega: \Psi \to \Omega$ that maps such manifolds to orthogonal, straightened non-linear, one-dimensional manifolds in $\Psi$. For example, two samples of two different analytes (e.g., $\vec{v}_2 \perp \vec{v}_1$, $\vec{v}_1, \vec{v}_2 \in V$) may map to two independent vectors (e.g., $\vec{s}_1, \vec{s}_2 \in \Psi$). Mapping $\omega$ may map $\vec{s}_1$ and $\vec{s}_2$ to $\vec{q}_1, \vec{q}_2 \in \Omega$ such that an angle between $\vec{q}_1$ and $\vec{q}_2$ is maximized. For example, $\Omega$ may be determined such that cosine distance $d(\vec{q}_1, \vec{q}_2)$ is minimized. When the manifolds corresponding to the different analytes in $\psi$ are already orthogonal, $\omega$ may reduce to the identity function. As discussed herein, $\omega$ may be expressed as a parametric function of some parameter set Y: $\vec{q} = \omega(\vec{s}; Y)$. Values for parameter set Y may be estimated using machine learning techniques, such as feedforward neural networks and Gaussian processes. In some embodiments, the mapping $\omega: \Psi \to \Omega$ fulfills the following conditions: $\omega$ is a continuous mapping between $\psi$ and $\Omega$, $\omega$ is bijective from $\Phi$ to $\Omega$, $\omega^{-1}$ is a continuous mapping between $\Omega$ and $\Psi$, and $\omega^{-1}$ is bijective from $\Omega$ to $\Psi$. The above conditions may follow from the homeomorphism between $\Omega$ and $\Psi$. Furthermore, function w may reduce the impact of noisy data, as w may map aligned vectors in $\Omega$ corresponding to noisy measurements of different analyte along orthogonal directions in $\Psi$.

In operations 260 and 270, the independent, aligned vectors generated in operation 250 can be applied to a third sub-model that relates the orthogonal, straightened representation $\Omega$ to the output representation V. In some embodiments, this third sub-model can include two component models. As described above, multiple component models may provide more flexibility and be easier to train than a single model providing the same functionality.

In operation 260, the first component model can be configured to align the orthogonal, straightened manifolds corresponding to varying concentrations of differing analytes with the standard basis vectors of $\mathbb{R}^M$ (e.g., from orthogonal, straightened representation 251 to standard basis representation 261, as depicted in FIG. 2B). For example, the first component model can be configured to implement a mapping $\tau: \Omega \to U$ that maps manifolds corresponding to varying concentrations of a single base analyte to the standard basis vectors $e_i$ of $\mathbb{R}^M$. For example, when the chemical sensing unit is configured to detect two analytes, samples including varying concentrations of a first analyte can lie on a first one-dimensional, straightened manifold in $\Omega$. Samples including varying concentrations of the second analyte can lie on a second one-dimensional, straightened manifold in $\Omega$, orthogonal to the first one-dimensional, straightened manifold. In this two-dimensional example, the first component model can map the first one-dimensional, straightened manifold to the standard basis vector $e_1 = [1\ 0]$ and map the second one-dimensional, straightened manifold to the standard basis vector $e_2 = [0\ 1]$. When the chemical unit is configured to detect additional relevant analytes, the representation $\Omega$ will contain more manifolds corresponding to these additional relevant analytes, which will be mapped to additional standard basis vectors $e_i$ of $\mathbb{R}^M$. As discussed herein, T may be expressed as a parametric function of some parameter set $\Pi$: $\vec{u} = \tau(\vec{q}; \Pi)$. Values for parameter set H may be estimated using machine learning techniques, such as feedforward neural networks and Gaussian processes. In some embodiments, $\tau$ may comprise one or more rotation matrices. The parameters comprising parameter set $\Pi$ may be values in the one or more rotation matrices.

In operation 270, the second component model can be configured to map from the manifolds corresponding to single analytes in U to linearized manifolds corresponding to single analytes in V (e.g., from standard basis representation 261 to output representation 271, as depicted in FIG. 2B). In some embodiments, for example, doubling a concentration of an analyte in the environment may not result in a doubling of a corresponding value in U. Accordingly, the first component model can be configured to implement a mapping $\eta$: $U \to V$ that maps the standard basis representation U to output representation V. The relationship between concentrations of analytes in the environment and values in output representation V may be linear. For example, a doubling of a concentration of an analyte in the environment may result in a doubling of a corresponding value in V. As discussed herein, $\eta$ may be expressed as a parametric function of some parameter set $\Gamma$: $\vec{v} = \eta(\vec{u}; \Gamma)$. Values for parameter set $\Gamma$ may be estimated using machine learning methods, such as feedforward neural networks and Gaussian processes.

The above described process 200 is intended to be exemplary and non-limiting. In some embodiments, one or more acts of process 200 may be omitted. For example, act 230 may be omitted when the Z' is not embedded in Z. As an additional example, acts 240 and 250 may be omitted when the one-dimensional manifolds corresponding to the varying concentrations of single analytes do not require straightening or orthogonalization. Furthermore, the association of one-dimensional manifolds in $\Omega$ with analytes and the generation of output representation V can be combined into a single act. In this single act, each element of V may be described by a unique directional vector $\hat{s}_k$ in $\Psi$. The collection of M vectors $\hat{s}_k$ may define a basis for $\Psi$. This basis may be orthogonalized and transformed to the standard basis of $\mathbb{R}^M$ using, standard linear algebra techniques, and described by the linear transformation $\vec{u} = G\vec{s}$. This linear transformation may be more generally denoted as a parametric function of G: $\vec{u} = \rho(\vec{s}, G)$. In the case where the vectors $\hat{s}_k$ already form an orthogonal basis, G reduces to the identity function. Under the linear transformation G, the vector $\hat{u}_k = G\hat{s}_k$ becomes a scalar multiple of a standard basis vector $\hat{e}_k$, and $\vec{v}$ may be recovered by a mapping $\eta_2: U \to V$ that maps to output representation V. As discussed herein, $\eta_2$ may be expressed as a parametric function of some parameter set $\Gamma$: $\vec{v} = \eta_2(\vec{u}; \Gamma)$. Values for parameter set $\Gamma$ may be estimated using machine learning techniques, such as feedforward neural networks and Gaussian processes. In this example, in contrast to the example provided above with respect to acts 240 and 250, labels identifying the samples in $\vec{u}$ corresponding to the axes in V may be required to generate G and $\eta_2$.

Figure 3:
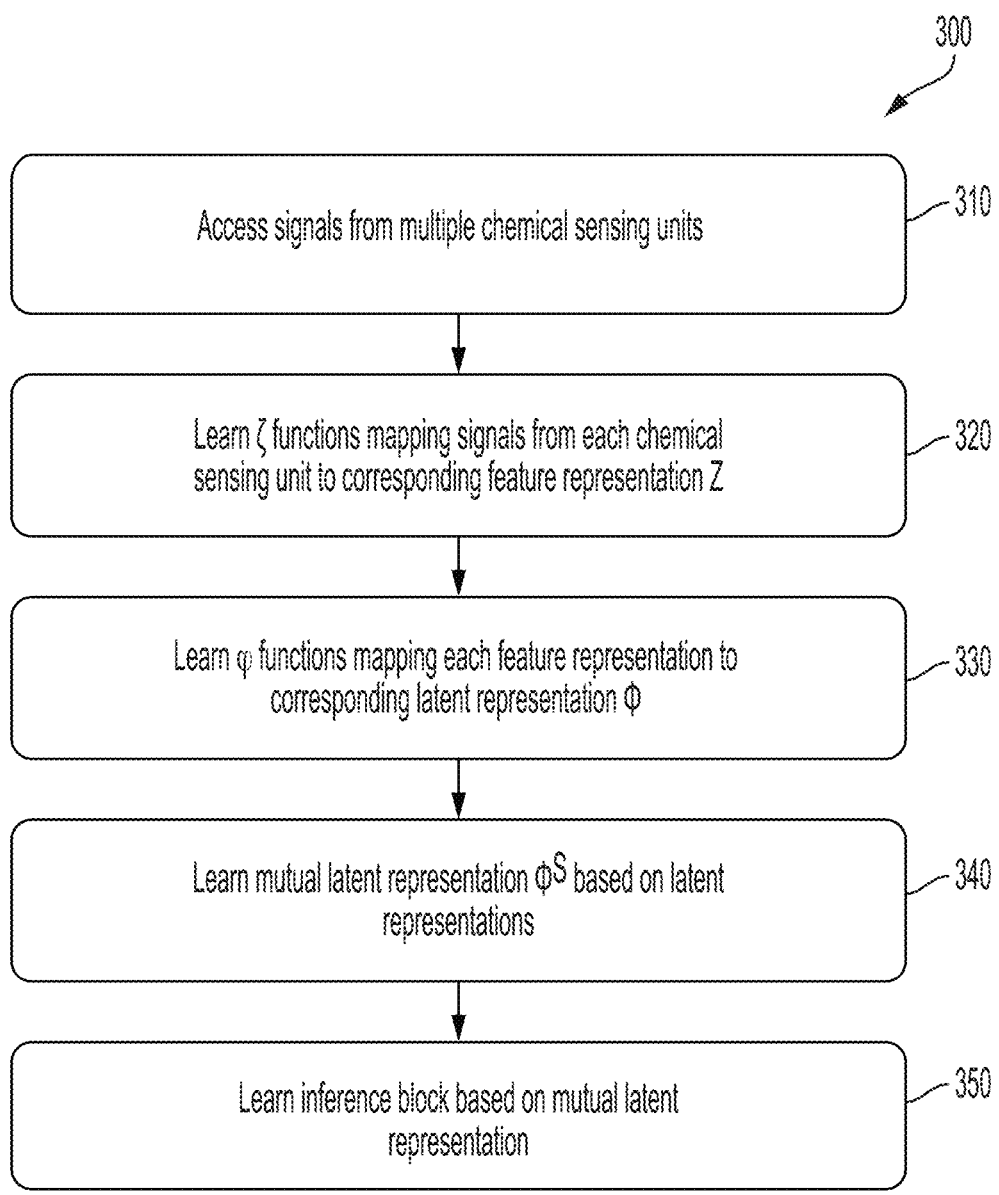
FIG. 3 depicts an exemplary process for training a set of models using data from multiple chemical sensing units.

FIG. 3 depicts an exemplary process 300 for training a set of models using data from multiple chemical sensing units (e.g., chemical sensing units 100, as shown in FIG. 1C). As described herein at least with respect to FIGS. 2A and 2B, process 300 is implemented by sequentially applying one or more models to the data from multiple chemical sensing units. The one or more models may include parameters and/or hyper-parameters stored in a storage device of the chemical sensing system. In some embodiments, the parameters are learned using machine learning techniques, examples of which are described with respect to FIGS. 2A and 2B. A chemical sensing system configured to apply the sequence of one or more models according to the learned parameters and/or hyper-parameters to output signals may, for example, infer a chemical composition of an environment from the output signals.

Figure 4:
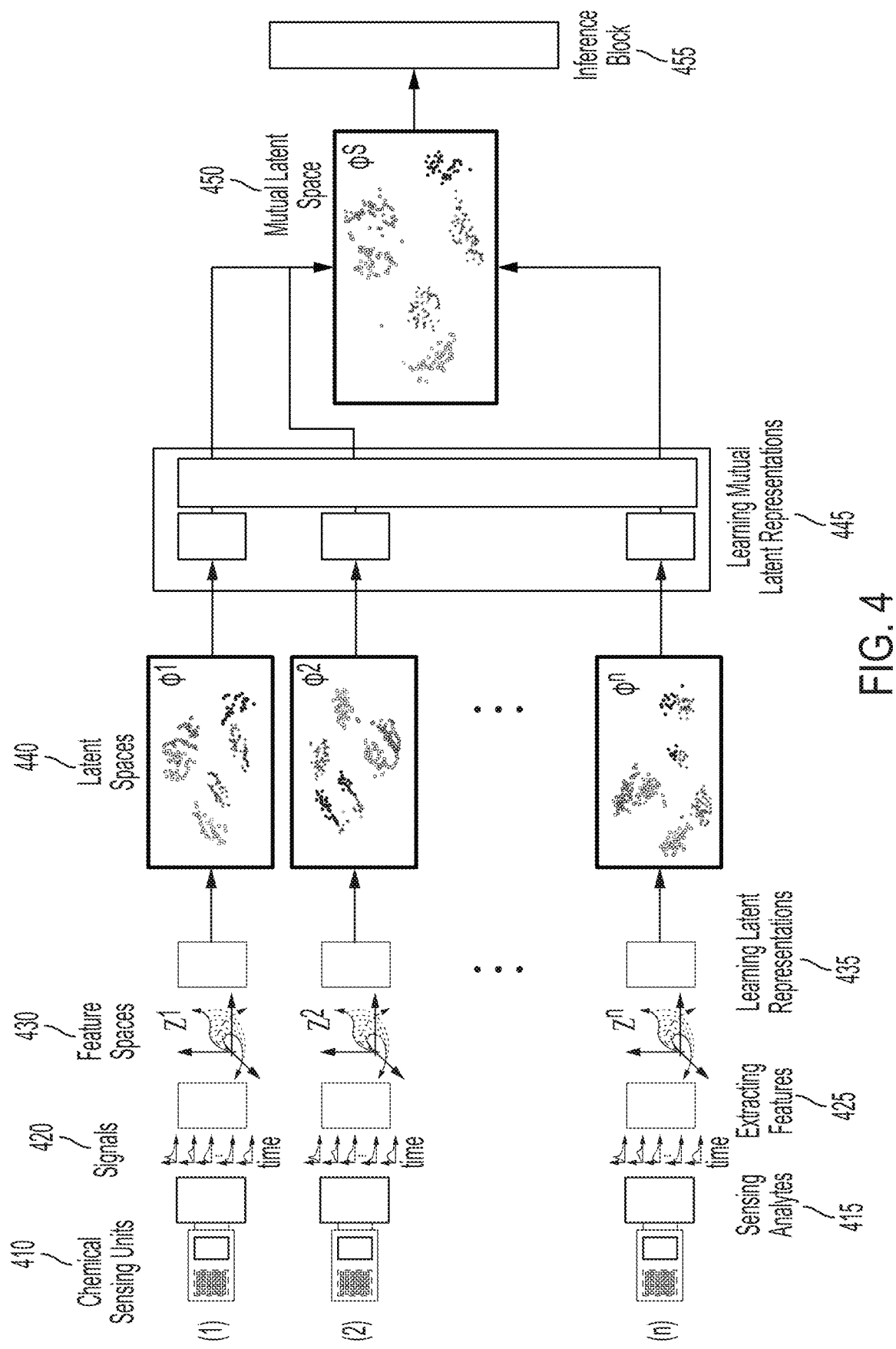
FIG. 4 is a diagram depicting an exemplary set of models which may be trained according to the process of FIG. 3.

In process 300, the series of models may be expressed as a series of functions, referred to herein as mappings, that transform input chemical sensor signals into a series of corresponding representations, also referred to herein as spaces, that may be used to generate an inference about the corresponding semantics (e.g., a concentration of one or more analytes) in the environment of the chemical sensing units. FIG. 4 is a flow diagram that illustrates an exemplary series of representations corresponding to the process of FIG. 3. The flow diagram also illustrates a pipeline of information processing, in accordance with some embodiments, when multiple chemical sensing units are used in the same application(s) and hence are exposed to the same set/type of odors (across chemical sensing units). In some embodiments, the example processes illustrated in FIGS. 3 and 4 may omit certain operations and/or representations, may repeat certain operations, and/or may integrate operations and representations associated with any suitable process described herein, including, but not limited to, those described with respect to FIGS. 2A and 2B.

Returning to FIG. 3, the process 300 begins at operation 310 with accessing signals from multiple chemical sensing units. Operation 310 may correspond to operation 210 of FIG. 2A, with multiple chemical sensing units producing output signals which are then accessed for further processing. FIG. 4 further illustrates an example of operation 310, where the chemical sensing units 410, after sensing of analytes 415, produce output signals 420. The chemical sensing units 410 may be configured as shown in FIG. 1C, and may be configured to communicate with one another and/or with an external storage device. The signals accessed at operation 310 may be accessed from the external storage device, received directly from the chemical sensing units 410, or accessed in any other suitable manner. The signals may be in any suitable format, examples of which are described herein at least with respects to FIG. 2A.

For notational convenience, with respect to FIGS. 3 and 4, let x represent the signals output from a chemical sensing unit. If M is the number of signals produced by the sensor array associated with that chemical sensing unit, then $x=(x_1, x_2, \ldots, x_M)$ such that x ranges in an M dimensional space S. As described herein, a chemical sensing unit may produce signals, for example, when exposed to an analyte sample within its environment over time, resulting in a time-dependent M dimensional output. Let A(t) represent the chemical composition (e.g., concentrations of various analytes) within the environment at time t. According to some embodiments, the chemical composition of the environment before the sample was taken (e.g., pre-stimulus) may be considered $A^1$ and the chemical composition of the environment after the sample is taken (e.g., post-stimulus) may be considered as $A^2$.

At operation 320, a $\zeta$ function may be learned for each chemical sensing unit, mapping signals output from the chemical sensing unit to a corresponding feature representation Z. Operation 320 may correspond to operation 220 of FIG. 2A, in which signals from a chemical sensing unit are mapped to a feature representation, applied over multiple chemical sensing units. As shown in FIG. 4, operation 320 may extract features 425 from signals 420 to produce feature spaces 430 corresponding to the chemical sensing units 410. A $\zeta$ function learned according to operation 320 may produce a descriptor z(t), represented as a K dimensional vector within the feature representation Z, based on the signals output from a chemical sensing unit at time t. A descriptor z(t) may be considered a unique numeric representation of the output signals in the feature space Z. Represented mathematically, a descriptor may be produced by applying $\zeta$ over the sensor outputs x for a time window of size $\Delta t$, such that $z(t)=\zeta(x_{[t-\Delta t, t]})$. Expanding this expression over the K dimensions of the feature space, yields: $z(t)=(z_1(t), z_2(t), \ldots, z_K(t))=(\zeta_1(x_{[t-\Delta t, t]}), \zeta_2(x_{[t-\Delta t, t]}), \ldots, \zeta_K(x_{[t-\Delta t, t]}))=\zeta(x_{[t-\Delta t, t]})$. Thus the $\zeta$ functions learned at operation 320 may be considered maps with the range in Z and the domain in the concatenation of space S and the time dimension.

In some embodiments, some signals may not influence the feature representation and thus may be associated with zero weighting in the calculation of descriptor z(t). Similarly, although a fixed continuous period of time may be used for the time window in the expressions above, in some cases discontinued and/or variable periods of time may be used.

As described herein, A(t) may represent the semantics associated with the signals x(t), where $z(t)=\zeta(x(t))$ is the correspondent descriptor, and where the following characteristics hold:
 (i) By changing the chemical composition of the environment from $A(t_1)$ to $A(t_2)$ gradually with a continuous process, the correspondent descriptor in the Z space will change gradually over a continuous one-dimensional curve from $z(t_1)$ to $z(t_2)$.
 (ii) If $A(t_1)$ is considered closer to $A(t_2)$ than a chemical composition $A(t_3)$, then with respect to at least one distance metric that describes the chemical composition, the correspondent descriptors, $z(t_1)$ will be closer to $z(t_2)$ than $z(t_3)$. The Z space in many cases is a metric space.

The above-mentioned characteristics may lead to the formation of manifolds in the feature representation Z, which may be referred to herein as Z'. The data distributions (e.g., clusters of data) within Z may be a transformation of the measured signals into the feature space. The data distributions may be dense where there are more samples available from the correspondent semantics. The dense data distributions form manifolds, which may be learned for representation of the semantics. The map $\zeta$ is often a homeomorphism.

The set of all possible values of a variable under certain constraints may be referred to herein as a manifold. A chemical sensing unit designed in accordance with some embodiments may produce values from measured signals in a continuous range, resulting in the formation of continuous data distributions and manifolds. The manifolds may correspond to various chemical compositions, such that areas that are closer in the formed manifolds may correspond to more similar chemical compositions or smells.

The constraints that limit the measured signals of a chemical sensing unit may be governed by one or more of (i) the characteristics of the chemical composition of the environment, (ii) the chemo-physical attributes of the binding process between the chemical molecules and the receptors on the chemical sensing unit, (iii) the chemo-physical characteristics of the receptors and the design of the sensory array of the chemical sensing unit, (iv) the design of the chemical sensing unit hardware (e.g., the type, the shape and structure of the headspace), (v) the design of the sampling process (e.g., the manner in which samples are collected and/or exposed to the chemical sensing unit, which may be referred to herein as a sniffing process), and (vi) the electronics design.

In some embodiments, the areas of the Z space within which implausible measurements exist (e.g., because of the constraints) may be carved out, leading to the formation of subspaces of Z (e.g., the manifolds). Thus the dynamics of the relations between variables may define the shape of the manifolds. Manifold learning is a technique for learning the underlying dynamics at different points spanning the Z space and the data distributions. Through manifold learning, the effect of the constraints on the captured data, and consequently on the distributions that form the manifolds, may be implicitly learned.

The measurements from the chemical sensing unit and the $\zeta$ function that maps the measured signals to the Z space determine the distribution of data in the Z space and the shape of the underlying manifolds in the Z space. In some embodiments, the manifolds are learned by assessing their similarities (e.g., distance in the Z space) through neighborhood embedding methods. This step can be learned, for example, via unsupervised manifold learning methods (e.g., Uniform Manifold Approximation and Projection (UMAP)).

$\zeta^1, \zeta^2 \ldots, \zeta^n$ may be defined as functions that map the measured signals from the chemical sensing units 1 through n to the corresponding Z space, $Z^1, Z^2, \ldots, Z^n$ respectively. Although the chemical sensing units may have manufacturing differences that lead to variations between signals output from each chemical sensing unit, each may be configured to include, within the output signals, information for interpreting the semantics of their shared environment. This information may include, for example, the presence of chemicals (e.g., one or more chemicals for which the sensors of the sensing unit are designed) and their concentrations (e.g., chemical composition or odors of interest) with the environment. The corresponding $\zeta$ functions may be developed to extract the information content from the output signals via a first model or sub-model for each chemical sensing unit. Therefore, there may be a one-to-one map between the semantics and the Z spaces for each sensing unit, which implies existence of an isomorphism (bijective homeomorphism) between any pair of Z spaces.

As shown in FIG. 4, the learned $\zeta$ maps for extracting the informative descriptors (e.g., feature vectors) from the measured signals produce feature spaces that include data distributions mapping to the semantics associated with the corresponding application. Since the semantics of the application may be unique, the information content of datasets acquired across chemical sensing units should theoretically be similar. When chemical sensors of similar types (e.g., types sensitive to a particular chemical or family of chemicals) are used across chemical sensing units, similar information content of the datasets across the chemical sensing units may lead to formation of similar manifolds.

Each Z space may be a metric space and distance in the Z space represents the similarity of the semantics (e.g., chemical compositions) within the application. As shown in FIG. 4, due to the characteristics of the metric space, clusters form. Each cluster may represent a manifold, a dense data structure where information about common semantics may be concentrated. When the semantics are similar across sensing units, the formation of clusters in the feature spaces Z may also be similar.

As discussed above, multiple instances of a same sensing unit may have variations in chemo-physical characteristics of the individual sensors introduced, for example, during manufacturing. Such differences may end up yielding some variations in the output of the sensors upon exposure to an environment having the same chemical composition. In addition to the measured signal from two replications of the same sensing units being different, the (learned) $\zeta$ maps for extracting information from the measured signals may also be different.

Returning to FIG. 3, at operation 330 a $\varphi$ function may be learned by mapping each feature representation Z to a corresponding latent representation $\Phi$. Operation 330 may correspond to operation 230 of FIG. 2A, in which a feature representation is mapped to a latent representation, applied over multiple feature representations. As shown in FIG. 4, latent representation learning 425 may be applied to the feature spaces 420 to produce latent spaces 440.

For each chemical sensing unit, the descriptors (e.g., feature vectors) generated in a Z space can be applied to a second model or sub-model that relates the feature representation Z to a latent representation $\Phi$ to generate latent vectors corresponding to the feature vectors. A latent representation $\Phi$ can be an inner product space. The latent representation $\Phi$ can be of the same dimension as the manifold Z'. As a non-limiting example, when Z', which represents the manifolds within Z, is a plane embedded in Z, the latent representation $\Phi$ may be a two-dimensional space (e.g., a latent representation, as depicted in FIG. 4). The second sub-model may implement a mapping $\varphi: Z \rightarrow \Phi$. As discussed herein, $\varphi$ may be expressed as a parametric function of some parameter set $\Lambda$: $\vec{p} = \varphi(\vec{z}; \Lambda)$. Values for parameter set $\Lambda$ may be estimated using representation learning techniques such as employing a feed forward neural network and recurrent neural networks. In some embodiments, the mapping $\varphi: Z \rightarrow \Phi$ fulfills the following conditions: $\varphi$ is a continuous mapping between Z' and $\Phi$, $\varphi$ is bijective from Z' to $\Phi$, $\varphi^{-1}$ is a continuous mapping between $\Phi$ and Z', and $\varphi^{-1}$ is bijective from $\Phi$ and Z'. The above conditions may follow from the homeomorphism between Z' and $\Phi$. The functions $\varphi^1, \varphi^2, \ldots, \varphi^n$ may be defined to map the feature spaces to corresponding $\Phi$ spaces, $\Phi^1, \Phi^2, \ldots, \Phi^n$ respectively.

Although the Z spaces may have distribution differences, each includes information for interpreting the application-driven semantics in the environment, including, for example, to detect chemicals of interest and their concentrations. The information for interpreting the application-driven semantics may also be present in the latent representations. Thus, as shown in FIG. 4, clusters may form in the latent spaces representing this information. These clusters may be learned with unsupervised manifold learning, or any other suitable technique, as described herein. Across chemical sensing units, some clusters (e.g., in FIG. 4, the clusters represented by the open squares and the open stars; the clusters represented by the filled circles and plus symbols; the clusters represented by the open circles and the × symbols) may be located next to each other in the latent spaces. When two clusters are close together in a latent space, their correspondent semantics (e.g., chemical compositions) may be similar with respect to the collected observations.

Returning to FIG. 3, at operation 340 a mapping from the $\Phi$ spaces $\Phi^1, \Phi^2, \ldots, \Phi^n$ to a mutual latent space $\Phi^S$ may be learned. As shown in FIG. 4, mutual latent representation learning 445 may be applied to latent spaces 440 to produce the mutual latent space 450. In some embodiments a one-to-one map may exist between each of the $\Phi$ spaces $\Phi^1, \Phi^2, \ldots, \Phi^n$, which in turn implies existence of an isomorphism (bijective homeomorphism) between any pair of the P spaces. Therefore, a (reference) mutual latent space $\Phi^S$ may be considered that has an isomorphism to each of $\Phi^1, \Phi^2, \ldots, \Phi^n$ spaces.

In some cases, the functions $\varphi^1, \Phi^2, \ldots, \Phi^n$ may be defined such that $\varphi^i = \varphi^j$ for all i, j, thereby mapping the feature spaces to their correspondent $\Phi$ spaces such that $\Phi^i = \Phi^j$ for all i, j. It follows then that $\Phi^i = \Phi^S$ for all i since the correspondent $\Phi$ spaces are identical. Therefore, in such cases, $\varphi^i$ directly maps the feature space to the (reference) mutual latent space $\Phi^S$.

Additionally or alternatively, a (reference) mutual latent space $\Phi^S$ that has an isomorphism to each of $\Phi^1, \Phi^2, \ldots, \Phi^n$ spaces may be considered. To build $\Phi^S$, a map can be trained that transfers any of the $\Phi^1, \Phi^2, \ldots, \Phi^n$ spaces to another of them (referred to as the reference latent space), or a new $\Phi^S$ can be created that has a separate isomorphism with respect to each of the $\Phi^1, \Phi^2, \ldots, \Phi^n$ spaces. The individual maps may transform the corresponding $\Phi^i$ spaces to temporary representations $\Phi^{i\prime}$, that are often sparse and homomorphic to $\Phi^i$. The shared map may optimize the presentation of a global map $\Phi^S$, for example with respect to minimal redundancy (e.g., same cardinality with $\Phi^i$) and maximal relevance for a particular application (e.g., encoding information relevant to particular inferences, such as analyte composition or concentrations, which may be generated based on $\Phi^S$).

Returning to FIG. 3, at operation 350 an inference block may be learned based on the mutual latent representation. As shown in FIG. 4, the inference block 455 may map from values in the mutual latent space 450 to inferences, which may represent the results of an identification, quantification, or predication task regarding the semantics detected by the chemical sensing units 410. For example, an inference may be a quantification of the concentration of one more analytes within a sample. In some embodiments, the inference block may be a feed forward neural network, a support vector machine, a recurrent neural network, a long-short-term-memory neural network, or any other suitable statistical model for generating inferences.

Figure 5:
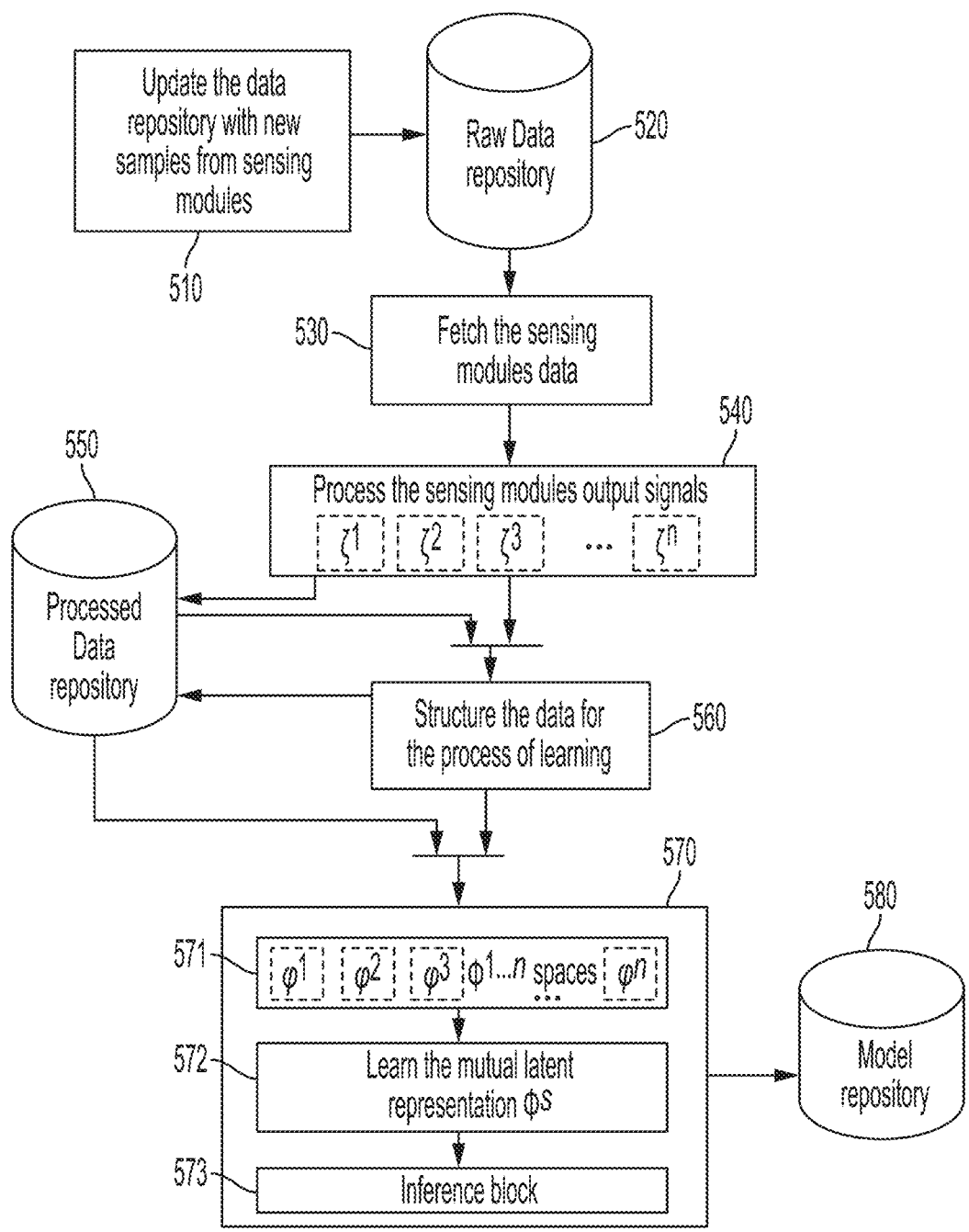
FIG. 5 is a diagram depicting an exemplary system architecture that may be used when training models according to the techniques described herein.

FIG. 5 depicts an exemplary system architecture for a chemical sensing system comprising many chemical sensing units. The chemical sensing units may be configured as shown in FIG. 1C, with multiple chemical sensing units being in communication with one another and/or an external storage medium. It should be appreciated that the system architecture of FIG. 5 may be implemented with any appropriate hardware and/or software, as described herein. For example, the operations shown in FIG. 5, including storing data, accessing data, and processing data, may be performed as part of a computer program implemented on one or more processors storing instructions on a non-transitory storage medium. The system architecture of FIG. 5 may additionally or alternatively be implemented in a distributed computing environment, including, for example, a cloud computing environment.

At operation 510, data from the chemical sensing units may be stored in a data repository 520 (which may correspond to external storage device 190 in FIG. 1C, in some embodiments). The data may include values representing signals output by the chemical sensing units (e.g., the "sensing modules" shown in operations 510 and 520). The data additionally or alternatively may include metadata representing information about the corresponding analytes, their concentrations, the environment, and/or the configuration or type of chemical sensing units being used. In some embodiments, the metadata may be associated with some or all of the signals output by the chemical sensing units. The metadata may be used to determine labels corresponding to the values representing signals output by the chemical sensing units. A set of the labels and the values to which they correspond may comprise a training dataset, which may be used to train at least one model as described herein.

At operation 530, the data stored in the data repository may be accessed (e.g., "fetched") from the data repository. This operation may correspond, for example, to operation 310 of process 300 in FIG. 3, and may be carried out according to any of the techniques described herein at least with respect to FIG. 3. In some embodiments, operation 530 may be carried out by one or more processors, which may, for example, include a server external to the chemical sensing units.

At operation 540 the data accessed at operation 530, including the values representing the signals from each chemical sensing unit, may be processed. More particularly, the processing may comprise extracting features from the data, according to any of the techniques described herein at least with respect to FIGS. 2A-2B, 3-4, and 6-8. The processing at operation 530 may include training a model that maps the data to a feature representation. As shown in FIG. 5, the results of operation 530 may be maps $\zeta^1, \zeta^2, \ldots, \zeta^n$. These maps may be represented in any suitable manner, including, for example, as values within one or more data structures (e.g., numeric weights within a matrix). Optionally the processed data (e.g., a representation of the maps $\zeta^1, \zeta^2, \ldots, \zeta^n$) may be stored in processed data repository 550. Processed data repository 550 may be a shared data repository with raw data repository 520 or may be a separate data repository.

At operation 560, the processed data may be structured for subsequent processing, including, for example, a learning process 570. Structuring the processed data at operation 560 may comprise, for example, combining the processed data received from operation 530 with data accessed from processed data repository 550, which may include previously stored processed data (e.g., maps $\zeta^1, \zeta^2, \ldots, \zeta^n$). The resulting structured data may be stored in the processed data repository 550, and may be accessed, for example, during subsequent instances of operation 560.

The structured data, which may be received from operation 560 and/or accessed from the processed data repository 550, may then be provided as input to the learning process 570. The learning process 570 may be carried out according to any of the techniques described herein at least with respect to FIGS. 3-4 and 6-8, and may include training one or more models via machine learning techniques, as described herein. The results of the learning process 570 may include trained models that may be represented in any suitable format, including as values in one or more data structures (e.g., as weights in a matrix or matrices).

As part of learning process 570, at operation 571, functions $\varphi^1, \varphi^2, \ldots, \varphi^n$ may be learned, with the functions mapping data from the feature representations Z to corresponding latent representations $\Phi$. The $\varphi^1, \varphi^2, \ldots, \varphi^n$ functions may be learned according to any of the techniques described herein at least with respect to FIGS. 2A-2B, 3-4, and 6-8.

At operation 572, a mutual latent representation may be learned according to any of the techniques described herein at least with respect to FIGS. 3-4 and 6-8.

At operation 573, an inference block may be learned according to any of the techniques described herein at least with respect to FIGS. 3-4, and 6-8. Operation 573 may serve to assign context to the mutual representation space, allowing inferences regarding the semantics to be drawn based on mutual representation values. The inference block of the information processing unit may be a feed forward neural network or a support vector machine (SVM), for example.

In some embodiments, the results of learning system 570, which may include trained models as described herein, may be stored in a model repository 580. Model repository 580 may be shared with processed data repository 550 and/or raw data repository 520 or may be a separate data repository.

Figure 6:
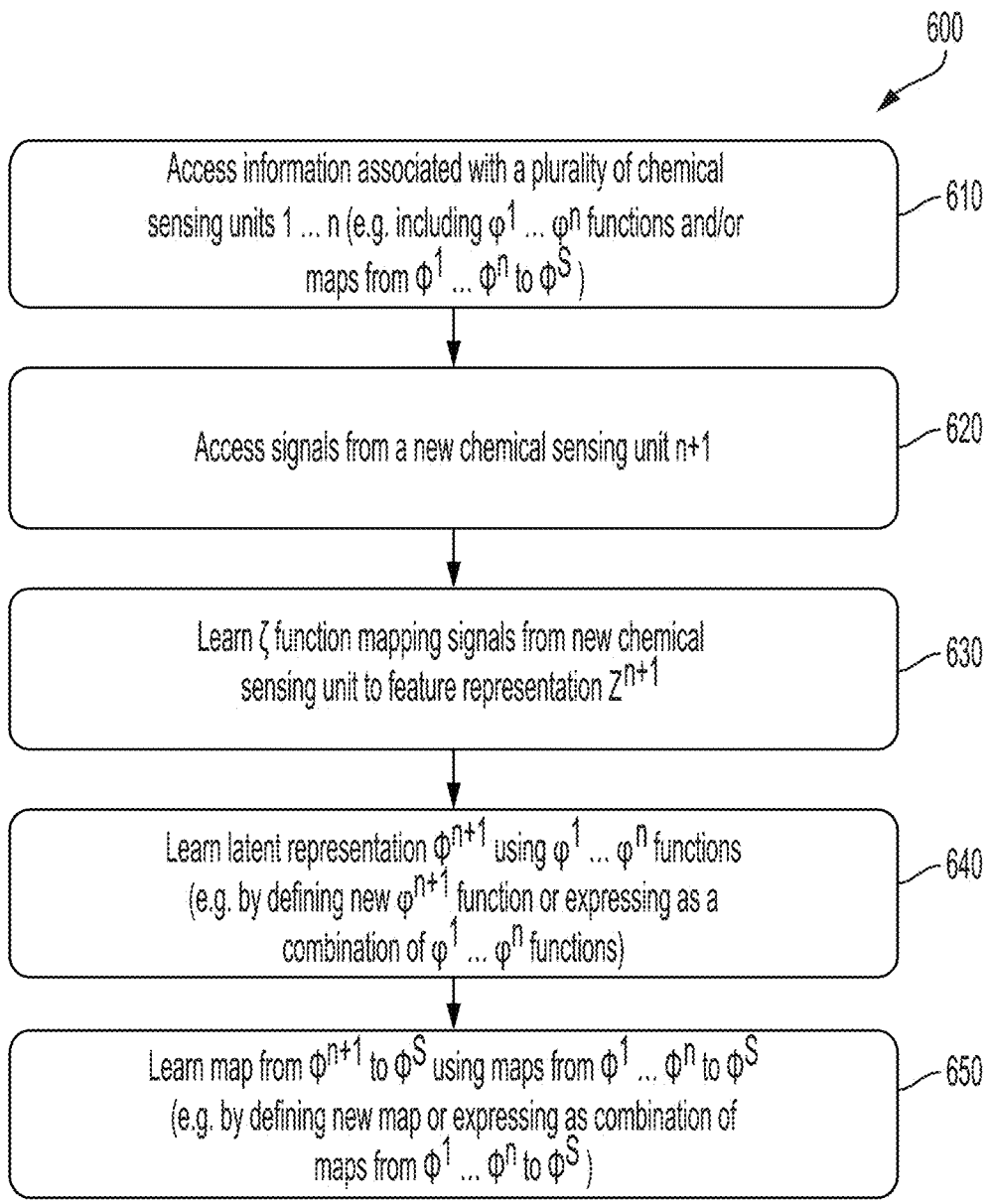
FIG. 6 depicts an exemplary process for training a set of models using data from previously trained models, and data from at least one additional chemical sensing unit.
Figure 7:
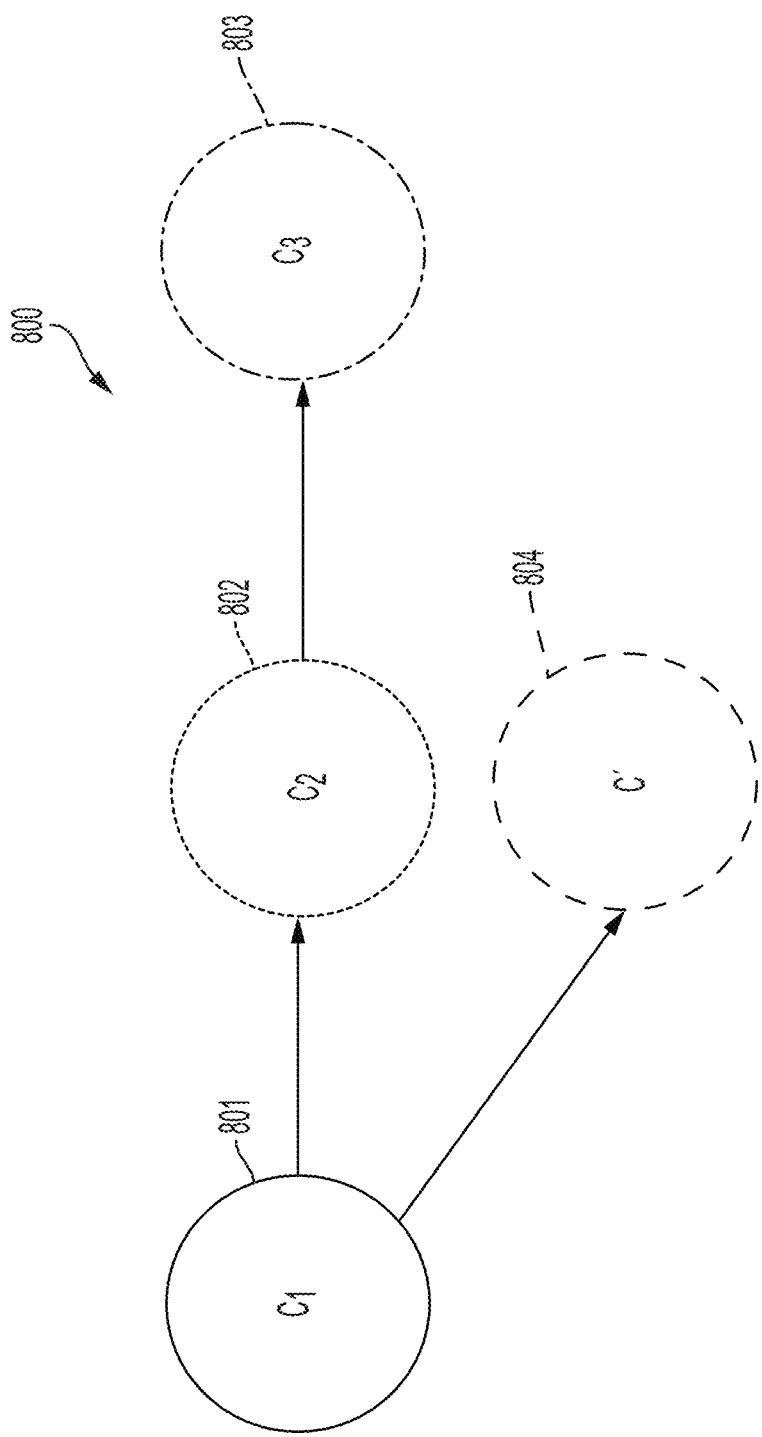
FIG. 7 depicts an exemplary process for training a set of models using sequential information about previously trained models, and data from at least one additional chemical sensing unit.

FIGS. 6 and 7 present techniques for leveraging available training data for a new chemical sensing unit, together with information regarding previously-trained models associated with other chemical sensing units, in order to train one or models associated with the new chemical sensing unit. For example, in some embodiments, a limited quantity of training data may be available (e.g., in the form of output signals from the new chemical sensing unit labelled according to the corresponding semantics) and model information from previously-trained models may be leveraged to achieve accurate results despite the limited quantity of training data. In some embodiments, the information regarding previously-trained models may be accessed from a storage medium such as the model repository 580. In some embodiments, the information regarding previously-trained models may be stored by the chemical sensing units themselves, and may be accessed accordingly.

FIG. 6 depicts an exemplary process for training a set of models using data from previously-trained models and data from at least one additional chemical sensing unit (e.g., a new chemical sensing unit). The exemplary process of FIG. 6 involves learning a map that transforms the output signals of the new chemical sensing unit to a mutual latent representation with limited training data. More particularly, as part of learning a latent representation corresponding to the new chemical sensing unit, information representing the latent representations of the previously-trained models may be leveraged to learn the new latent representation. This may further facilitate the calculation of parameters mapping the new latent representation to the latent representation to the mutual latent representation.

Unlike supervised learning techniques in which a generalization task may be learned by training a model using many labeled observations (e.g., for every chemical sensing unit), semi-supervised learning can be leveraged to learn patterns (e.g., the maps for a new sensing unit) with a reduced quantity of labeled observations. In general, the accuracy of the learned maps increases with more observations; however, an acceptable level of accuracy can be achieved by using limited observations and leveraging the existence of the maps learned for chemical sensing units that include similar chemical sensors. In some experiments described in more detail below, an 80% accuracy was achieved for a new (e.g., previously unseen) chemical sensing unit by training the model(s) associated with an existing chemical sensing system with a reduced quantity of data (2% of the dataset used to initially train the system) from the new chemical sensing unit.

In FIG. 6, process 600 begins at operation 610, with accessing information associated with 1 . . . n chemical sensing units. These chemical sensing units may be incorporated as a portion of a chemical sensing system for which models (e.g. as described herein at least with respect to FIGS. 3-4) have already been trained.

At operation 620, signals from a new chemical sensing unit n+1 are accessed. These signals may have corresponding labels, and together the signals and labels may comprise a data set that can be used as training data for training one or more models associated with the new chemical sensing unit. The quantity of training data associated with the signals accessed from the n+1 chemical sensing unit at operation 620 may be less than the quantity of training data used to train the models associated with the n chemical sensing units (e.g., less than 10%, such as 5%, or 2%).

At operation 630, a $\zeta$ function mapping the accessed signals from the new chemical sensing unit n+1 to a feature representation $Z^{n+1}$ may be learned. Operation 630 may be carried out according to the techniques for feature extraction described herein at least with respect to FIGS. 2A-2B and 3-4. Operation 630 may alternatively or additionally use the information associated with the n chemical sensing units, accessed at operation 610, to learn the new function.

At operation 640, a latent representation $\Phi^{n+1}$ is learned for the chemical sensing unit n+1 associated with the feature space $Z^{n+1}$ from operation 630. In some embodiments, a new map $\varphi^{n+1}$ may be learned, where $\varphi^{n+1}: Z^{n+1} \to \Phi^{n+1}$, according to any of the techniques described herein at least with respect to FIGS. 2A-2B and 3-4. In some embodiments, information representing the functions $\varphi^1, \varphi^2, \ldots, \varphi^n$ associated with the chemical sensing units 1 . . . n may be used as part of learning the $\varphi^{n+1}$ map. In some embodiments, the map from $Z^{n+1} \to \Phi^{n+1}$ may be expressed as combination of the functions $\Phi^1, \varphi^2, \ldots, \varphi^n$.

At operation 650, a map from the latent representation $\Phi^{n+1}$ to a mutual latent representation $\Phi^s$ is learned. In some embodiments, there is a one-to-one map between all $\Phi$ spaces. The previously-learned maps associated with the chemical sensing units 1 . . . n from $\Phi^{1 \cdots n}$ to $\Phi^s$ may be used to learn the isomorphism map from $\Phi^{n+1}$ to the reference latent space $\Phi^s$. The map from $\Phi^{n+1}$ to $\Phi^s$ can be learned by combining the previously-learned maps for the chemical sensing units 1 . . . n or as a new map.

In some embodiments, a partially labeled dataset may provide weak supervision to map individual latent spaces $\Phi^i$ to the final mutual latent space $\Phi^S$, where the following objectives direct the construction of a loss function used for the learning process:

- The manifolds should be correspondent and hence the neighborhood characteristics of the $\Phi^i$ will be equivalent to the neighborhood characteristics of $\Phi^S$. For example, the mapped representation of close/far samples in $\Phi^i$ to the $\Phi^S$ will stay close/far.
- The semantics of the latent representations $\Phi^i$ should match the semantics in $\Phi^S$ so that latent variables in $\Phi^i$ spaces with same or very similar semantics will match latent variables in $\Phi^S$ that are close to each other (respecting the similarity of their semantics) and latent variables in $\Phi^i$ spaces with different or very distinguishable semantics will match latent variables in $\Phi^S$ that are far each other (respecting the dissimilarity of their semantics).

According to some embodiments, there may be instances in which the chemical composition of the environment at a particular point in time depends on the sequence of chemical compositions during at least one previous point in time. In such instances, the transitions from one chemical composition to another may also be learned and represented in the mutual latent representation to improve information processing capabilities.

FIG. 7 illustrates a sequential relationship described by transitions from one data distribution to another data distribution. Sequential relationships can be captured by sequential models for inference purposes. Sequential relationships may also provide information about the transitionary states (e.g., data distributions in a latent representation). Thus the sequential relationships may provide support and information about the semantics, and may therefore facilitate building isomorphism between the $\Phi^i$ and $\Phi^S$.

In FIG. 7, $C_1$, $C_2$, $C_3$, and C' represent four different data distributions. The traverse from C1 to C' represents a semantic that is distinguishable from the semantic associated with the transition from C1 to C2 and then C3. For example, consider a sequential relationship in a latent representation $\Phi^i$, that involves a traverse through three distributions; this may correspond to the same sequential relationship in another latent space $\Phi^i$ that traverses through three distributions. The correspondence between sequential relationships across chemical sensing units, supports the likelihood of correspondence of the involved distributions in the transitions respectively. Hence the semantics of unlabeled distributions in a latent representation would be tied to the semantics of the correspondent distributions in the other latent representations considering the sequential relationships.

Figure 8:
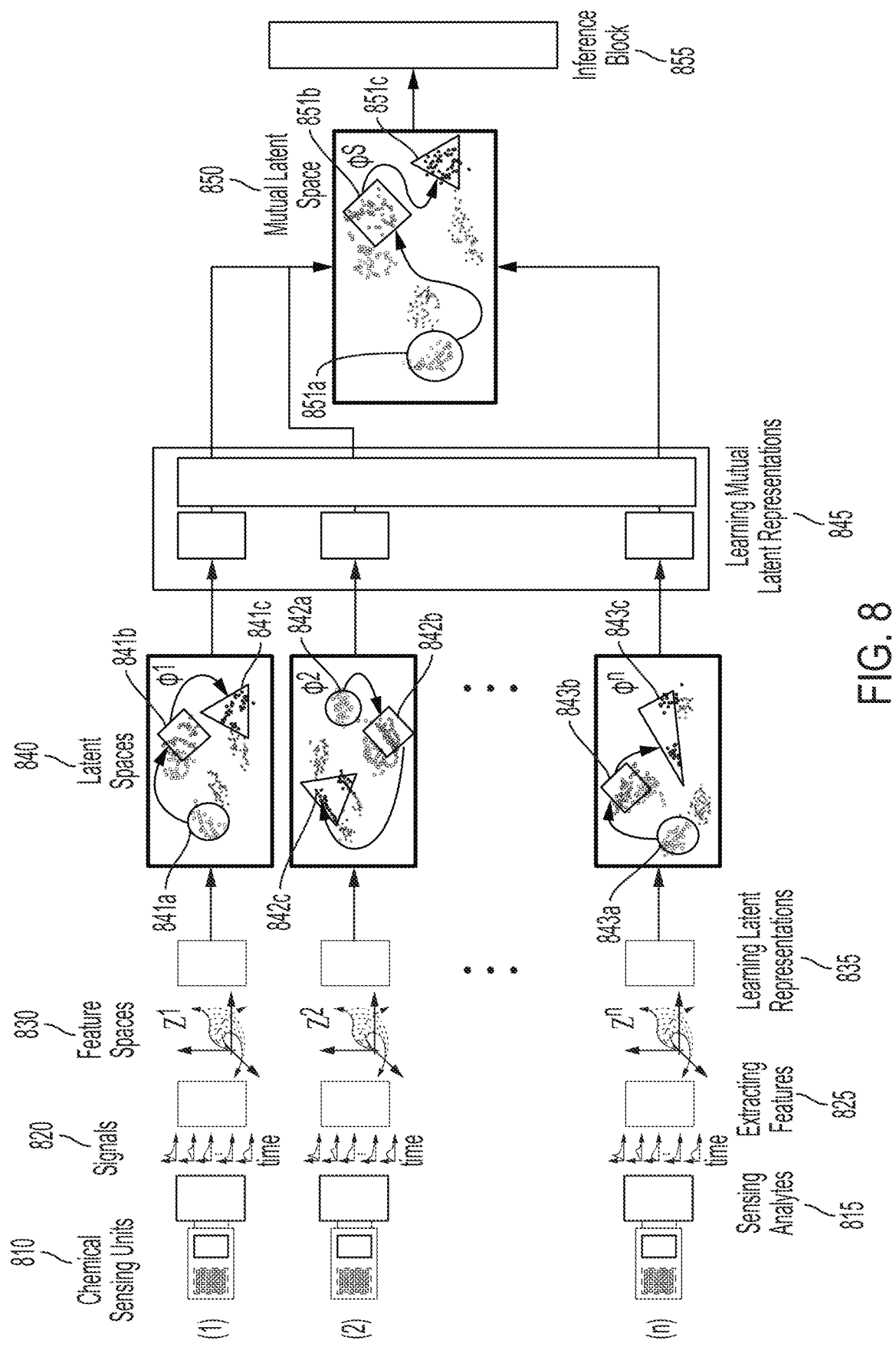
FIG. 8 is a diagram depicting an exemplary set of models which may be trained according to the process of FIG. 7.

FIG. 8 further explains a technique for learning sequential relationships in accordance with some embodiments. As shown in the figure, sequential relationships may arise between data distributions in the latent representations 840: for example, 841a→841b→841c in the latent space $\Phi^1$; 842a→842b→842c in the latent space $\Phi^2$; and 843a→843b→843c in the latent space $\Phi^3$. When the chemical sensing units 810 are exposed to the same semantics, it follows that the resulting sequential relationships should have a correspondence. As shown in FIG. 8, the mutual latent space $\Phi^S$ 850 expresses a corresponding sequential relationship 851a→881b→851c. Given latent representations having corresponding sequential relationships across chemical sensing units (e.g., where the chemical sensing units include chemical sensors that were designed/used for similar applications) the correspondence may be leveraged during the process of building the isomorphism from $\Phi^i$ to $\Phi^S$.

Additionally or alternatively, sequential relationships may be leveraged as part of the inference block. The inference block of the information processing unit should be able to model sequential relationships, and recurrent neural networks and long-short-term-memory based networks could be used to build such inference blocks, for example.

Figure 9:
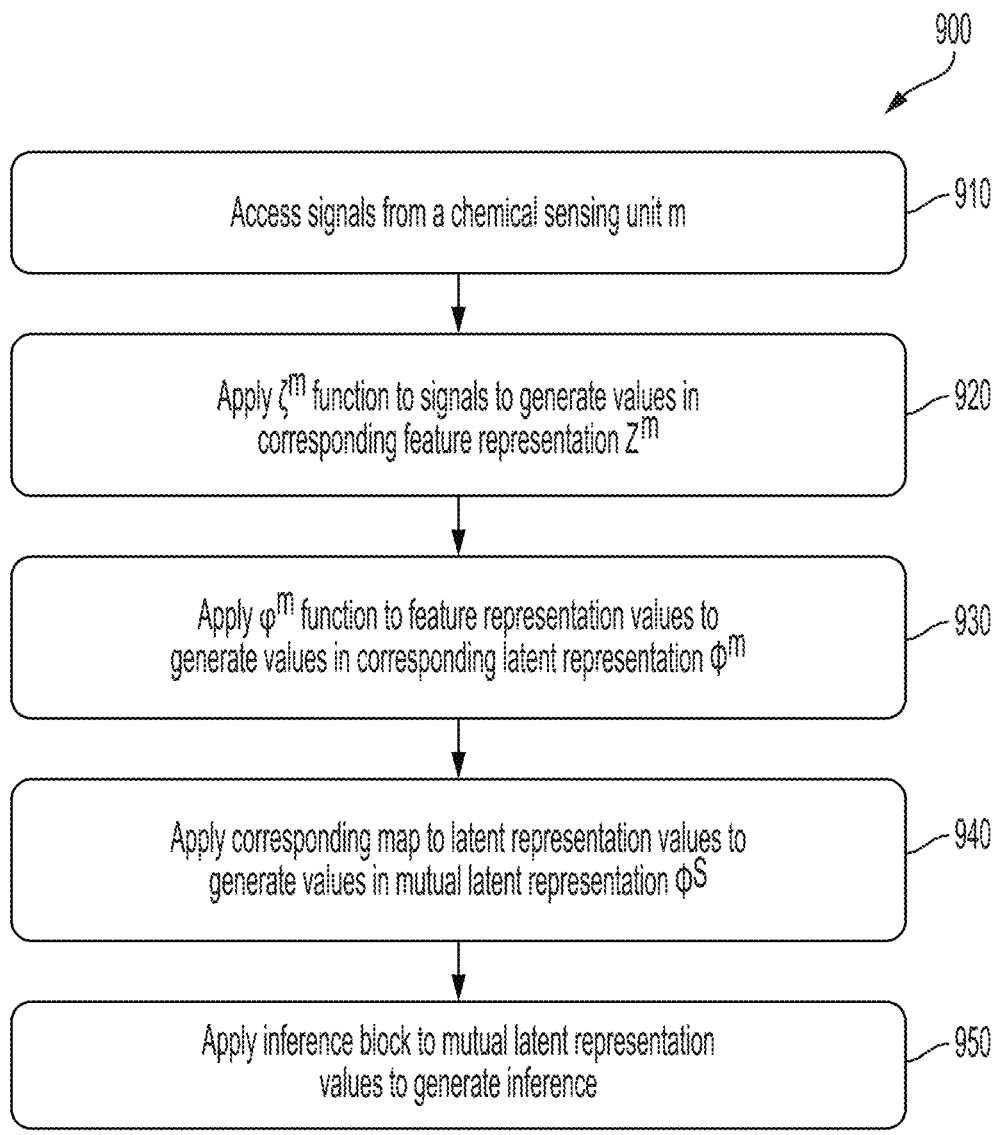
FIG. 9 is an exemplary process for using a trained set of models to generate an inference based on input signals from a chemical sensing unit.

FIG. 9 depicts an exemplary process 900 for using a trained set of models to generate an inference based on input signals from a chemical sensing unit. A set of models, trained according to the techniques described herein at least with respect to FIGS. 3-4 and 6-8, may be used to generate an inference based on new data acquired from a chemical sensing unit. The set of models may be trained on data acquired from chemical sensing unit(s) as described herein, or pre-trained models may be accessed from a storage medium (e.g., model repository 580).

At operation 910, new data may be accessed in the form of signals from a chemical sensing unit m. The new data may be in any suitable format, as described herein. The new data may be associated with the current semantics of the corresponding environment.

At operation 920, a feature vector may be generated by applying the appropriate $\zeta^m$ function (e.g., via a model of the set of models) to the signals accessed at operation 910. The result may be a descriptor in $Z^m$ space, reflecting the features extracted from the signals.

At operation 930, the feature vector may be provided as input to a function $\varphi^m$ (e.g., via a model of the set of models) that transforms the values in $Z^m$ into values in the latent representation $\Phi^m$.

At operation 940, the values in the latent space $\Phi^m$ may be mapped to the mutual latent representation $\Phi^s$.

Figure 10:
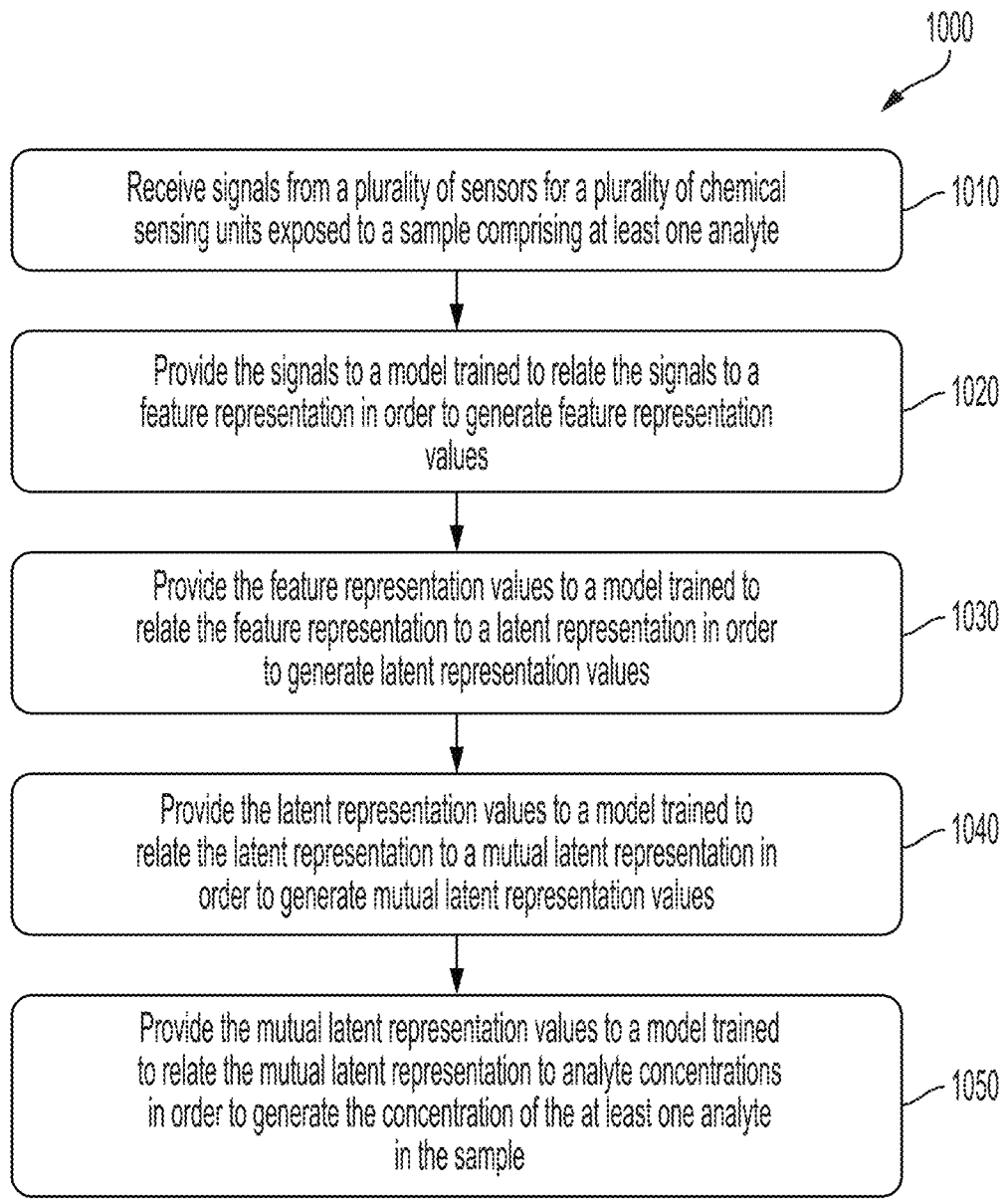
FIG. 10 is an exemplary process for using a trained set of models to determine a concentration of an analyte in a sample based on input signals from a plurality of chemical sensing units.

At operation 950, the inference block generates an inference based on the values in the mutual latent representation. As described herein, the inference may include identification, quantification, and prediction results FIG. 10 is an exemplary process for using a trained set of models to determine a concentration of an analyte in a sample based on input signals from a plurality of chemical sensing units. A set of models, trained according to the techniques described herein at least with respect to FIGS. 3-4 and 6-8, may be used to generate an inference based on new data acquired from a chemical sensing unit. The set of models may be trained on data acquired from chemical sensing unit(s) as described herein, or pre-trained models may be accessed from a storage medium (e.g., model repository 580).

At operation 1010, new data may be accessed in the form of signals from a chemical sensing unit having been exposed to at least one analyte of interest within a sample. The new data may be in any suitable format, as described herein.

At operation 1020, a feature vector may be generated by applying a model of the set of trained models to the signals accessed at operation 1010. The result may be a descriptor (e.g., feature values) reflecting the features extracted from the signals.

At operation 1030, the feature vector may be provided as input to a model of the set of models that transforms the values in the feature vector into values in the latent representation.

At operation 1040, the values in the latent representation may be mapped to the mutual latent representation, At step 1050, the inference block generates an inference based on the values in the mutual latent representation. In the example of FIG. 10, the inference is a concentration of at least one analyte in the sample to which the sensors of the chemical sensing unit were exposed.

Figure 11B:
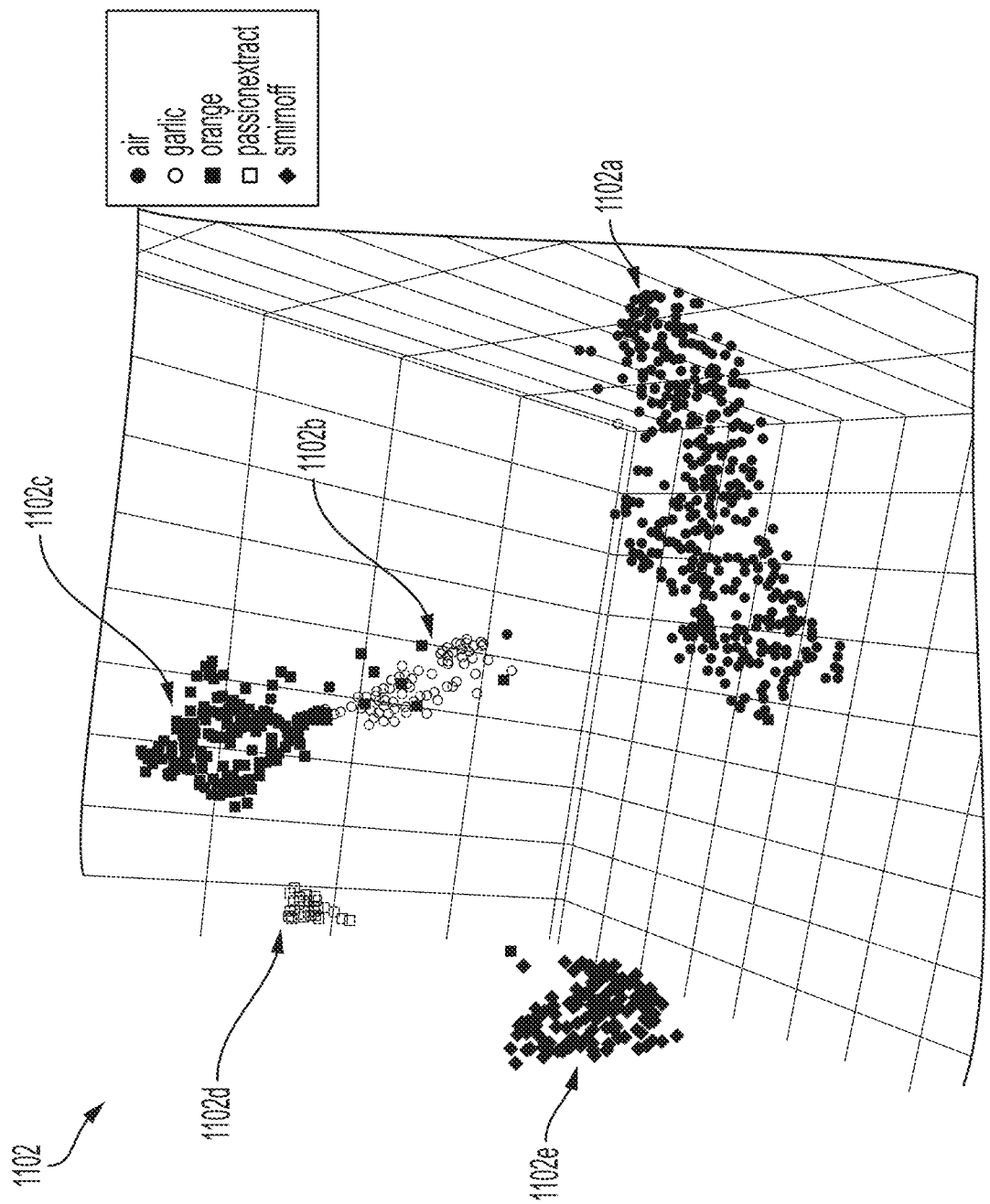
Figure 11C:
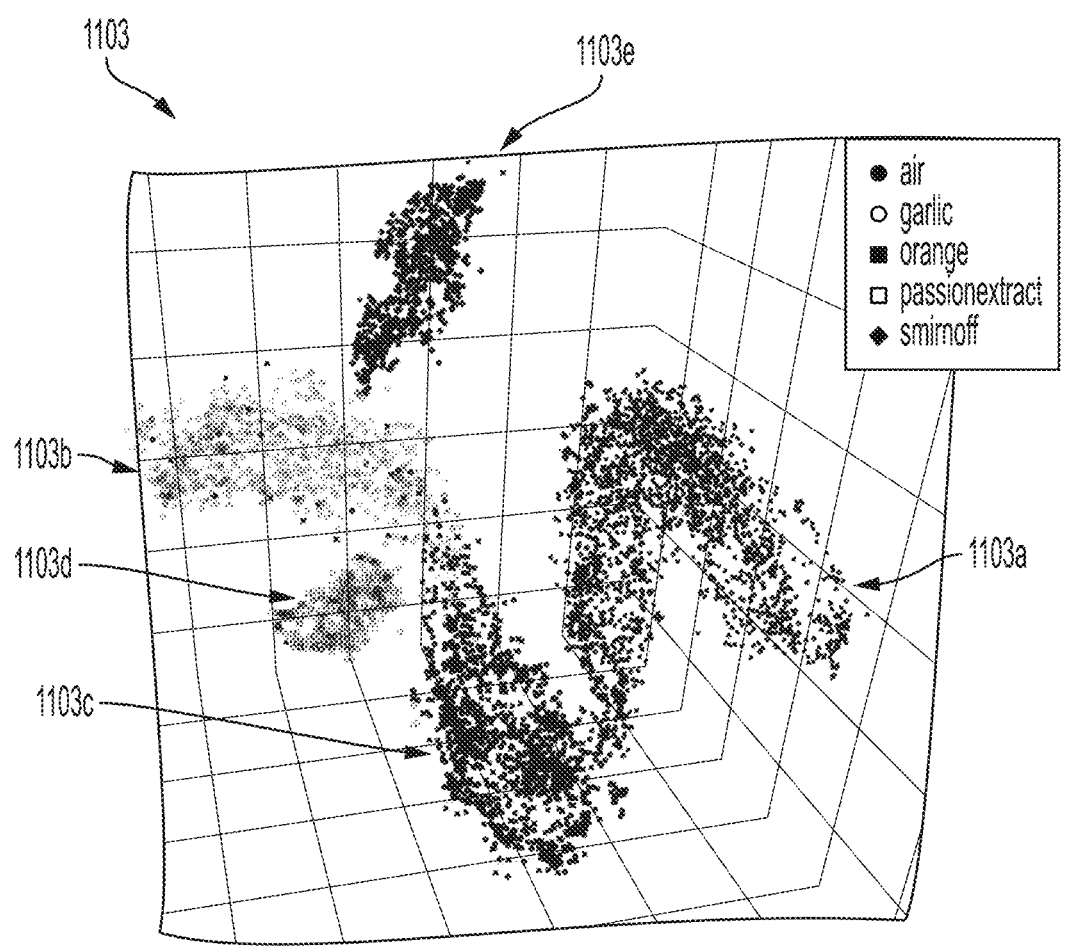

FIGS. 11A, 11B, and 11C relate to a non-limiting, exemplary implementation of some of the techniques as described herein, carried out over a proprietary data set. In this example, the dataset includes values representing signals (e.g., the time-dependent responses) of eight chemical sensing units for a total of 11,000 chemical samples from five analytes: air, oranges, garlic cloves, Smirnoff vodka, and passionfruit extract. Each time-dependent response may be referred to herein as a cycle, and may include 32 time-series data, corresponding to the 32 chemical sensors of the chemical sensing units, respectively.

In this example, the chemical sensing units may be situated within a device known as a 'sniffer', which may contain a mechanism for drawing gaseous samples into an area above the sensing elements for a period of controlled exposure. The gaseous sample may be drawn through a nozzle, which may be held near the analyte for delivery to the sensing elements. Each cycle may be composed of: a baseline period, during which the background time-dependent response is established; an exposure period, during which the sensing unit is exposed to the analyte and time-dependent responses are collected; and a recovery period, during which the time-dependent responses recover toward the background time-dependent response.

In FIGS. 11A through 11C, the analytes air, garlic, orange, passion extract, and Smirnoff vodka are represented by filled circles, open circles, filled squares, open squares, and filled diamonds, respectively. FIGS. 11A and 11B depict the latent representations $\Phi^i$ (more particularly, $\Phi^1$ and $\Phi^2$) generated by the mappings $\varphi^i$: $Z^i \rightarrow \Phi^i$ learned for each sensing unit, according to the techniques described herein. FIG. 11 C depicts a (reference) mutual latent space $\Phi^S$ which, in this example, is isomorphic to each of the $\Phi^1, \Phi^2, \ldots, \Phi^8$ latent spaces that correspond respectively to the eight sensing units.

In the illustrated example, the data set, comprising 11,000 cycles across eight devices, is utilized to showcase the output at various stages of the techniques described herein. The chemical sensing units employed in this example produce time-dependent responses with a sampling rate of 1 Hz; over 40 seconds, each sensing element outputs a series of readings throughout a cycle for a total of 40 such readings. Each reading in the cycle is represented by $f_1$ which is a 32-element reading normalized with respect to a baseline vector, $\beta$. More specifically, each reading $\alpha_i$ is divided elementwise by the baseline vector, $\beta$, followed by a subtraction of the value 1:

$$f_i = \begin{bmatrix} f_1 \\ f_2 \\ \vdots \\ f_{32} \end{bmatrix}, \alpha_i = \begin{bmatrix} \alpha_1 \\ \alpha_2 \\ \vdots \\ \alpha_{32} \end{bmatrix}, \beta = \begin{bmatrix} \beta_1 \\ \beta_2 \\ \vdots \\ \beta_{32} \end{bmatrix} \text{ where } f_i = \frac{\alpha_i}{\beta_i} - 1$$

In this example, the resulting descriptor for a single cycle is a matrix of size (40, 32), and the dataset comprises 11,000 such cycles. Thus the resulting set of descriptors is a matrix of size (11000, 40, 32). The set of descriptors may be further divided into eight descriptor sets of size ($n_i$, 40, 32) where $n_i$ is the number of samples collected via sensing unit i.

In this example, a mapping $\varphi^i: Z^i \rightarrow \Phi^i$ is learned for each chemical sensing unit. Two non-limiting embodiments of the mapping to the mutual latent space are considered in this example. In the first embodiment, the mapping $\varphi^i: Z^i \rightarrow \Phi^i$ is decoupled from the mapping of each $\Phi^i$ to $\Phi^S$ followed by a mapping of all $\Phi^i$ to $\Phi^S$, such that $\varphi^i$ and $\varphi^j$ for $i,j \in \{1, 2, \ldots n\}$ are not necessarily equal. In the second embodiment, the functions $\Phi^1, \Phi^2, \ldots, \Phi n$ can be learned such that $\varphi^1 = \varphi^2 = \ldots = \varphi^n$, thereby directly mapping each $Z^i$ to $\Phi^S$.

For this example, in either embodiment, convolutional neural networks may be deployed to transform data associated with each cycle into k-dimensional descriptors (where k in this example is equal to 256). The first embodiment may use unique convolutional neural networks for each chemical sensing unit to generate the descriptor (e.g., a feature vector) followed by manifold learning for a reduction of each descriptor to a latent representation (e.g., a three-dimensional vector). An additional neural network may then be used to learn the mapping of each three-dimensional vector into the mutual latent space.

In the second embodiment, a single convolutional neural network may learn the mapping directly using the entire data set. The mappings $\varphi^i: Z^i \rightarrow \Phi^i$ are learned such that $\varphi^1 = \varphi^2 = \ldots = \varphi^n$ and hence $\varphi^i$ maps $Z^i$ to $\Phi^S$ directly; i.e. the map from $\Phi^i$ to $\Phi^S$ is the identity map for $i \in \{1, 2, \ldots n\}$.

Vectors with three real-valued elements, such as those within the latent representations and mutual latent representations in this example, can be associated with points in three-dimensional space. Each vector with 256 elements can be associated with a point in 256-dimensional space. A transformed descriptor set of size (n, 256) can be associated with n points in 256-dimensional space (e.g., feature space Z). Points in this space may be close/further in proximity to one another if the corresponding semantics are more similar/dissimilar according to a given metric. For example, for a particular chemical sensing unit, two descriptors both corresponding to the semantics of an orange will be more similar than a descriptor corresponding to the semantics of an orange and a descriptor corresponding to the semantics of garlic.

In the following step of this example, manifold learning may be performed (e.g., using techniques such as t-SNE or UMAP). Manifold learning may be used to learn the underlying structure of the data space, thereby reducing the dimensionality of the data from 256 to 3, for example. It may be desirable that this method be non-parametric, and that it preserve the locality of nearby semantics in the original space after reducing the dimension. This may preserve embedded information regarding the chemical characteristics of the original data distributions. If two points in the original 256-dimensional space are close to one other, then the corresponding points may stay close in the new space created by reduction of dimensionality. Similarly, if two points in the original 256-dimensional space are far from one other, then the corresponding points may stay far from one another in the new space. In some embodiments, manifold learning is performed on the 256-dimensional output vectors, generating three-dimensional vectors in the correspondent space(s).

In the first embodiment, the learning of the map $\varphi^i: Z^i \rightarrow \Phi^i$ is performed separately for each chemical sensing unit (e.g., with separate convolutional neural networks). Manifold learning is then performed on the resulting 256-dimensional vectors in order to generate the corresponding three-dimensional vectors in $\Phi^i$ space. Consequently, the $\Phi^i$ spaces can be viewed in three dimensions for each chemical sensing unit.

FIG. 11A depicts a space $\Phi^1$ formed by feeding points associated with a first chemical sensing unit into the trained convolutional neural network described in the first embodiment, followed by manifold learning using t-SNE. As shown in the figure, clusters of points may arise corresponding to particular semantics in an environment (e.g., air cluster 1101a, garlic cluster 1101b, orange cluster 1101c, passionfruit extract cluster 1101d, and Smirnoff vodka cluster 1101e).

FIG. 11B depicts a space $\Phi^2$ formed by feeding points associated with a second chemical sensing unit into the trained convolutional neural network described in the first embodiment, followed by manifold learning using t-SNE. As shown in the figure, clusters of points may arise corresponding to particular semantics in an environment (e.g., air cluster 1102a, garlic cluster 1102b, orange cluster 1102c, passionfruit extract cluster 1102d, and Smirnoff vodka cluster 1102e). The clusters of FIG. 11B may be different from the clusters of FIG. 11A, but may correspond to the same semantics. For example, the first chemical sensing unit and second chemical sensing unit may be situated in the same environment (e.g. the same headspace), and may be exposed to the same analytes in the same concentrations.

In some cases, for the first embodiment, there may be no similarity constrains (e.g., no parameter sharing) in the process of building the $\varphi^i$ maps, and thus the maps $\varphi^i$ and the corresponding spaces need not be equivalent (i.e., $\Phi^1 \neq \Phi^2 \neq \ldots \neq \Phi^8$). In the second embodiment, the $\varphi^i$ maps are learned simultaneously, via the same convolutional neural network, and thus may be the same.

In the first embodiment, a neural network may then be used to learn the mutual representation $\Phi^S$, using as input the three-dimensional vectors produced as a result of manifold learning performed on the 256-dimensional output vectors produced by the trained convolutional neural networks associated with each chemical sensing unit. The second embodiment may use a single convolutional neural network trained on the entire dataset from all chemical sensing units to directly produce 256-dimensional vectors on which manifold learning can be performed to generate three-dimensional vectors in the space $\Phi^S$. In either case, the final three-dimensional vectors within the mutual latent space $\Phi^s$ such that points representing similar semantics may appear close to one another in space. In other words, the signals from the different chemical sensing units, which may be different from one another (e.g., due to variations in the manufacturing process), are mapped to the same space in the mutual latent representation.

FIG. 11C depicts a space $\Phi^S$ formed by feeding points associated with all the chemical sensing units of this example into the convolutional neural network described in the second embodiment, followed by manifold learning using t-SNE. In the first embodiment, a similar plot may be produced by plotting the output of the final neural network which learns a mapping from each $\Phi^i$ to the shared representation $\Phi^S$.

In the following step of this example, subsequent to the learning of the mutual representation, an appropriate inference model (e.g., corresponding to the inference block described elsewhere herein) may be chosen for the purpose of making inferences (e.g. discriminating between) analytes. Such models may include, but are not limited to, additional layers trained to classify samples, additional neural networks, or classical machine learning methods such as support vector machines. Such models may relate values in the mutual latent representation with a unique semantics that may correspond to a unique chemical composition (pure or complex chemical compositions).

Figure 12:
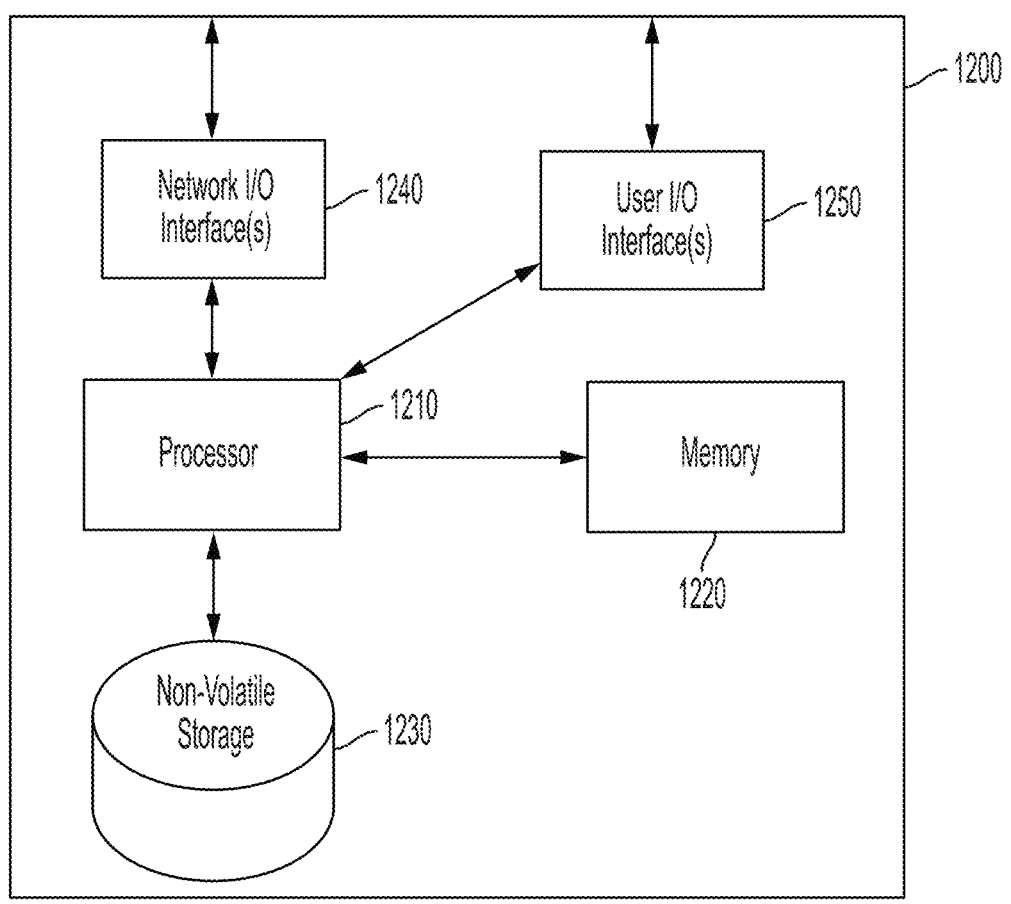
FIG. 12 depicts an illustrative implementation of a computer system that may be used in connection with some embodiments of the technology described herein.

An illustrative implementation of a computer system 1200 that may be used in connection with any of the embodiments of the technology described herein is shown in FIG. 12. The computer system 1200 includes one or more processors 1210 and one or more articles of manufacture that comprise non-transitory computer-readable storage media (e.g., memory 1220 and one or more non-volatile storage media 1230). The processor 1210 may control writing data to and reading data from the memory 1220 and the non-volatile storage device 1230 in any suitable manner, as the aspects of the technology described herein are not limited in this respect. To perform any of the functionality described herein, the processor 1210 may execute one or more processor-executable instructions stored in one or more non-transitory computer-readable storage media (e.g., the memory 1220), which may serve as non-transitory computer-readable storage media storing processor-executable instructions for execution by the processor 1210.

Computing device 1200 may also include a network input/output (I/O) interface 1240 via which the computing device may communicate with other computing devices (e.g., over a network), and may also include one or more user I/O interfaces 1250, via which the computing device may provide output to and receive input from a user. The user I/O interfaces may include devices such as a keyboard, a mouse, a microphone, a display device (e.g., a monitor or touch screen), speakers, a camera, and/or various other types of I/O devices.

The above-described embodiments can be implemented in any of numerous ways. For example, the embodiments may be implemented using hardware, software or a combination thereof. When implemented in software, the software code can be executed on any suitable processor (e.g., a microprocessor) or collection of processors, whether provided in a single computing device or distributed among multiple computing devices. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments described herein comprises at least one computer-readable storage medium (e.g., RAM, ROM, EEPROM, flash memory or other memory technology, CD-ROM, digital versatile disks (DVD) or other optical disk storage, magnetic cassettes, magnetic tape, magnetic disk storage or other magnetic storage devices, or other tangible, non-transitory computer-readable storage medium) encoded with a computer program (i.e., a plurality of executable instructions) that, when executed on one or more processors, performs the above-discussed functions of one or more embodiments. The computer-readable medium may be transportable such that the program stored thereon can be loaded onto any computing device to implement aspects of the techniques discussed herein. In addition, it should be appreciated that the reference to a computer program which, when executed, performs any of the above-discussed functions, is not limited to an application program running on a host computer. Rather, the terms computer program and software are used herein in a generic sense to reference any type of computer code (e.g., application software, firmware, microcode, or any other form of computer instruction) that can be employed to program one or more processors to implement aspects of the techniques discussed herein.

The foregoing description of implementations provides illustration and description, but is not intended to be exhaustive or to limit the implementations to the precise form disclosed. Modifications and variations are possible in light of the above teachings or may be acquired from practice of the implementations. In other implementations the methods depicted in these figures may include fewer operations, different operations, differently ordered operations, and/or additional operations. Further, non-dependent blocks may be performed in parallel.

It will be apparent that example aspects, as described above, may be implemented in many different forms of software, firmware, and hardware in the implementations illustrated in the figures. Further, certain portions of the implementations may be implemented as a "module" that performs one or more functions. This module may include hardware, such as a processor, an application-specific integrated circuit (ASIC), or a field-programmable gate array (FPGA), or a combination of hardware and software.

The invention claimed is:

1. A method of training a set of models used by a first chemical sensing unit to generate an inference about one or more chemical characteristics of an environment, wherein the training uses information associated with a plurality of chemical sensing units not including the first chemical sensing unit, the method comprising:
   accessing the information associated with the plurality of chemical sensing units, wherein the information relates a plurality of signals output from the plurality of chemical sensing units to a mutual latent representation, wherein the mutual latent representation provides a common representation space for the plurality of signals output from the plurality of chemical sensing units;
   accessing a training dataset including values representing signals output from the first chemical sensing unit; and
   training the set of models associated with the first chemical sensing unit, using the training dataset and the information associated with the plurality of chemical sensing units, wherein training the set of models comprises:
      training a first model of the set of models to relate the values representing the signals output from the first chemical sensing unit to a feature representation;
      training a second model of the set of models to relate the feature representation to a latent representation; and
      training a third model to relate the latent representation to the mutual latent representation,
      wherein the first chemical sensing unit is configured to use the trained first, second, and third models to generate an inference about one or more chemical characteristics of the environment based on the first chemical sensing unit sensing at least one analyte.

2. The method of claim 1, wherein the information associated with the plurality of chemical sensing units comprises:
   at least one mapping between a plurality of latent representations associated with the plurality of chemical sensing units and the mutual latent representation.

3. The method of claim 2, wherein training the third model to relate the latent representation to the mutual latent representation comprises:
   determining a mapping between the latent representation and the mutual latent representation using the at least one mapping between the plurality of latent representations and the mutual latent representation.

4. The method of claim 3, wherein the determined mapping between the latent representation and the mutual latent representation comprises a combination of multiple mappings of the at least one mapping between the plurality of latent representations and the mutual latent representation.

5. The method of claim 2, wherein the information associated with the plurality of chemical sensing units comprises:
   at least one mapping between a plurality of feature representations associated with the plurality of chemical sensing units and the plurality of latent representations associated with the plurality of chemical sensing units.

6. The method of claim 5, wherein training the second model to relate the feature representation to the latent representation comprises:
   determining a mapping between the feature representation and the latent representation, using the at least one mapping between the plurality of feature representations and the plurality of latent representations.

7. The method of claim 6, wherein determining the mapping between the feature representation and the latent representation comprises combining multiple mappings of the at least one mapping between the plurality of feature representations and the plurality of latent representations.

8. The method of claim 1, wherein training the first model comprises using a manifold learning technique, a neighborhood embedding technique, an unsupervised learning technique, or any combination thereof.

9. The method of claim 1, wherein the second model comprises a neural network model.

10. The method of claim 9, wherein the neural network model comprises a feed forward neural network, a recurrent neural network, a convolutional neural network, or any combination thereof.

11. The method of claim 10, wherein the third model comprises a neural network model.

12. The method of claim 11, wherein the neural network model comprises a feed forward neural network, a recurrent neural network, a convolutional neural network, or any combination thereof.

13. A system comprising:
   at least one computer processor;
   a first chemical sensing unit;
   a plurality of chemical sensing units not including the first chemical sensing unit; and
   at least one non-transitory computer-readable storage medium storing processor-executable instructions that, when executed by the at least one computer processor, cause the at least one computer processor to perform a method of training a set of models used by the first chemical sensing unit to generate an inference about one or more chemical characteristics of an environment, wherein the training uses information associated with the plurality of chemical sensing units, the method comprising:
   accessing the information associated with the plurality of chemical sensing units, wherein the information relates a plurality of signals output from the plurality of chemical sensing units to a mutual latent representation, wherein the mutual latent representation provides a common representation space for the plurality of signals output from the plurality of chemical sensing units;
   accessing a training dataset including values representing signals output from the first chemical sensing unit; and
   training the set of models associated with the first chemical sensing unit using the training dataset and the information associated with the plurality of chemical sensing units, wherein training the set of models comprises:
      training a first model of the set of models to relate the values representing the signals output from the first chemical sensing unit to a feature representation;
      training a second model of the set of models to relate the feature representation to a latent representation; and
      training a third model to relate the latent representation to the mutual latent representation,
      wherein the first chemical sensing unit is configured to use the trained first, second, and third models to generate an inference about one or more chemical characteristics of the environment based on the first chemical sensing unit sensing at least one analyte.

14. The system of claim 13, wherein the information associated with the plurality of chemical sensing units comprises:
   at least one mapping between a plurality of latent representations associated with the plurality of chemical sensing units and the mutual latent representation.

15. The system of claim 14, wherein training the third model to relate the latent representation to the mutual latent representation comprises:
   determining a mapping between the latent representation and the mutual latent representation using the at least one mapping between the plurality of latent representations and the mutual latent representation.

16. The system of claim 15, wherein the determined mapping between the latent representation and the mutual latent representation comprises a combination of multiple mappings of the at least one mapping between the plurality of latent representations and the mutual latent representation.

17. A chemical sensing system comprising:
   a first chemical sensing unit configured to:
      sense at least one analyte in a sample from an environment; and
      output signals generated as a result of sensing the at least one analyte;
   at least one computer processor; and
   at least one non-transitory computer-readable storage medium storing:

information representing a set of models trained using information associated with a plurality of chemical sensing units not including the first chemical sensing unit; and processor-executable instructions that, when executed by the at least one computer processor, cause the at least one computer processor to:

generate, using the information representing the set of models, an inference about one or more chemical characteristics of the environment based on the plurality of sensors sensing the at least one analyte in the sample by:

providing the signals as input to a first model of the set of models, wherein the first model is trained to relate the signals to a feature representation to generate feature representation values;

providing the feature representation values as input to a second model of the set of models, wherein the second model is trained to relate the feature representation to a latent representation to generate latent representation values;

providing the latent representation values as input to a third model of the set of models, wherein the third model is trained to relate the latent representation to a mutual latent representation to generate mutual latent representation values, wherein the mutual latent representation provides a common representation space for signals output from multiple chemical sensing units; and providing the mutual latent representation values as input to a fourth model of the set of models, wherein the fourth model is trained to relate the mutual latent representation to inferences to generate the inference about the one or more chemical characteristics of the environment based on the plurality of sensors sensing the at least one analyte in the sample.

18. The system of claim 17, wherein any two or more models of the set of models are combined into a single model.

19. The system of claim 17, wherein the one or more of the plurality of chemical sensing units output differing signals when exposed to a same analyte.

20. The system of claim 17, wherein the signals are stored in the at least one non-transitory computer-readable storage medium of the system.

21. The system of claim 17, wherein the instructions further cause the at least one processor to access the output signals directly from the plurality of sensors.

22. The system of claim 17, wherein the signals are stored in a second storage medium different from and external to the at least one non-transitory computer-readable storage medium.

23. The system of claim 22, wherein the instructions further cause the at least one processor to receive the signals from the second storage medium.

24. The system of claim 22, wherein the plurality of chemical sensing units include the second storage medium.

25. The system of claim 17, wherein the information representing the set of models comprises parameters learned from training using information associated with the plurality of chemical sensing units not including the first chemical sensing unit.

26. The system of claim 17, wherein the information representing the set of models is received from a second storage medium.

27. The system of claim 17, wherein the chemical sensing system includes the second storage medium.

28. The system of claim 17, wherein the at least one computer processor comprises a plurality of computer processors.

29. A method of generating an inference about one or more chemical characteristics of an environment by a chemical sensing system comprising a first chemical sensing unit and memory storing information representing a set of models trained using information associated with a plurality of chemical sensing units not including the first chemical sensing unit, the method comprising:

sensing, by the first chemical sensing unit, at least one analyte in a sample from the environment;

outputting, by the first chemical sensing unit, output signals generated as a result of sensing the at least one analyte;

generating, using the information representing the set of models, the inference about one or more chemical characteristics of an environment based on the plurality of sensors sensing the at least one analyte in the sample by:

providing the signals as input to a first model of the set of models, the first model trained to relate the signals to a feature representation to generate feature representation values;

providing the feature representation values as input to a second model of the set of models, the second model trained to relate the feature representation to a latent representation to generate latent representation values;

providing the latent representation values as input to a third model of the set of models, the third model trained to relate the latent representation to a mutual latent representation to generate mutual latent representation values, wherein the mutual latent representation provides a common representation space for signals output from multiple chemical sensing units; and providing the mutual latent representation values as input to a fourth model of the set of models, the fourth model trained to relate the mutual latent representation to inferences to generate the inference about the one or more chemical characteristics of the environment based on the plurality of sensors sensing the at least one analyte in the sample.

* * * * *